United States Patent
Porras De Francisco et al.

(10) Patent No.: US 11,253,499 B2
(45) Date of Patent: Feb. 22, 2022

(54) COMPOUNDS

(71) Applicants: GLAXOSMITHKLINE INTELLECTUAL PROPERTY DEVELOPMENT LIMITED, Middlesex (GB); BIOVERSYS AG, Basel (CH)

(72) Inventors: Esther Porras De Francisco, Tres Cantos (ES); Modesto Jesús Remuiñan-Blanco, Tres Cantos (ES); Marilyne Bourotte, Perenchies (FR); Benoit Deprez, Lille (FR); Geoffroy Dequirez, Lomme (FR); Nicolas Willand, Lille (FR)

(73) Assignees: GLAXOSMITHKLINE INTELLECTUAL PROPERTY DEVELOPMENT LIMITED, Middlesex (GB); BIOVERSYS AG, Basel (CH)

(*) Notice: Subject to any disclaimer, the term of this patent is extended or adjusted under 35 U.S.C. 154(b) by 0 days.

(21) Appl. No.: 16/639,292

(22) PCT Filed: Aug. 15, 2018

(86) PCT No.: PCT/EP2018/072145
§ 371 (c)(1),
(2) Date: Feb. 14, 2020

(87) PCT Pub. No.: WO2019/034702
PCT Pub. Date: Feb. 21, 2019

(65) Prior Publication Data
US 2020/0170997 A1    Jun. 4, 2020

(30) Foreign Application Priority Data
Aug. 16, 2017 (EP) .................... 17382571

(51) Int. Cl.
| | | |
|---|---|---|
| *A61K 31/397* | (2006.01) |
| *A61P 31/06* | (2006.01) |
| *A61K 31/4427* | (2006.01) |
| *A61K 45/06* | (2006.01) |
| *C07D 205/04* | (2006.01) |
| *C07D 401/04* | (2006.01) |
| *C07D 405/04* | (2006.01) |

(52) U.S. Cl.
CPC ........ *A61K 31/397* (2013.01); *A61K 31/4427* (2013.01); *A61K 45/06* (2013.01); *A61P 31/06* (2018.01); *C07D 205/04* (2013.01); *C07D 401/04* (2013.01); *C07D 405/04* (2013.01)

(58) Field of Classification Search
None
See application file for complete search history.

(56) References Cited

U.S. PATENT DOCUMENTS 9,073,912 B2 * 7/2015 Sheehan ............ A61K 31/4439

FOREIGN PATENT DOCUMENTS

| WO | WO 2010/052255 A1 | 5/2010 |
| WO | WO 2014/096369 A1 | 6/2014 |
| WO | WO 2014/096378 A1 | 6/2014 |

OTHER PUBLICATIONS

Marion Flipo, et al. "Ethionamide Boosters: Synthesis, Biological Activity, and Structure-Activity Relationships of a Series of 1,2,4-Oxadiazole EthR Inhibitors." Journal of Medicinal Chemistry, 54(8): 2994-3010 (Apr. 28, 2011).

* cited by examiner

*Primary Examiner* — Brian J Davis
(74) *Attorney, Agent, or Firm* — Robert H. Brink; Scott Young; Duke M. Fitch

(57) ABSTRACT

The invention relates to compounds of Formula (I) and their use in therapy, for example in the treatment of mycobacterial infections or in the treatment of diseases caused by *Mycobacterium*, such as tuberculosis.

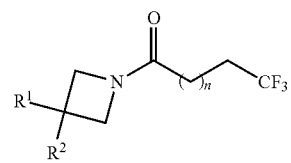

(I)

26 Claims, No Drawings

COMPOUNDS

This application is a § 371 of International Application No. PCT/EP2018/072145, filed 15 Aug. 2018, which claims the priority of EP 17382571.2, filed 16 Aug. 2017.

FIELD OF THE INVENTION

The invention relates to novel compounds, compositions containing them, and their use in therapy, for example in the treatment of mycobacterial infections or in the treatment of diseases caused by *Mycobacterium*, such as tuberculosis (also known as TB).

BACKGROUND TO THE INVENTION

Nearly ten million people are infected with tuberculosis (TB) each year, causing 1.5 million deaths each year, according to a report published by The World Health Organisation in 2014. Despite available treatments for tuberculosis, incidence of the disease still begins to rise, owing to infection by *Mycobacterium tuberculosis*, the causative bacterial agent for TB, becoming resistant to many of the first-line treatments such as isoniazid and rifampicin.

Ethionamide, a structural analogue of isoniazid, is frequently prescribed for the treatment of multidrug-resistant TB (MDR TB), which is as efficient as isoniazid. However, a disadvantage associated with the use of ethionamide is that in order to obtain an acceptable concentration of the drug in the blood, up to 1 g/day is required, which is associated with severe side effects including neurotoxicity and fatal hepatotoxicity. Therefore, there exists a need to reduce the clinical dose and exposure to ethionamide.

Consequently, one aim of the present invention is to provide novel compounds that are likely to be able to potentiate the activity of drugs used in the treatment of TB, in particular drugs that are activatable via the EthA pathway, such as ethionamide. A further aim of the present invention is to provide novel compounds for the treatment of TB.

SUMMARY OF THE INVENTION

In a first aspect of the present invention, there is provided a compound of Formula (I) or pharmaceutically acceptable salt thereof:

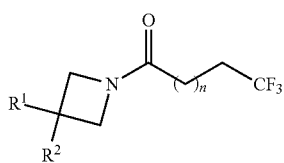

(I)

wherein
n is 1 or 2;
$R^1$ is hydrogen, fluoro, methyl or methoxy; and
$R^2$ is phenyl, pyridyl, $C_{3-6}$ cycloalkyl, piperidin-1-yl or tetrahydropyranyl,
wherein
phenyl and pyridyl are optionally substituted by one to three substituents independently selected from chloro, fluoro, cyano, $C_{1-3}$ alkyl optionally substituted by one or more fluoro, or $C_{1-3}$ alkoxy optionally substituted by one or more fluoro, and
cycloalkyl, piperidin-1-yl and tetrahydropyranyl are optionally substituted by one or two fluoro.

In a second aspect of the present invention, there is provided a compound of Formula (I) or pharmaceutically acceptable salt thereof, for use in therapy. In particular, for use in the treatment of tuberculosis, a mycobacterial infection or a disease caused by infection with a *Mycobacterium*.

In a third aspect of the invention, there is provided a method for the treatment of a mycobacterial infection in a mammal in need thereof, comprising administering to said mammal a therapeutically effective amount of a compound of Formula (I) or a pharmaceutically acceptable salt thereof.

In a fourth aspect of the invention, there is provided a method for the treatment of a disease caused by infection with a *Mycobacterium* in a mammal in need thereof, comprising administering to said mammal a therapeutically effective amount of a compound of Formula (I), or a pharmaceutically acceptable salt thereof.

In a fifth aspect of the invention, there is provided the use of a compound of Formula (I), or a pharmaceutically acceptable salt thereof, in the manufacture of a medicament for use in the treatment of a mycobacterial infection or a disease resulting caused by infection with a *Mycobacterium*.

In a sixth aspect of the present invention, there is provided a pharmaceutical composition comprising (a) a compound of Formula (I) or pharmaceutically acceptable salt thereof; and (b) a pharmaceutically acceptable excipient.

In a seventh aspect of the present invention, there is provided a combination of (a) a compound of Formula (I) or pharmaceutically acceptable; and (b) at least one other anti-mycobacterial agent.

DETAILED DESCRIPTION OF THE INVENTION

As described above, one aspect of the invention relates to a compound of Formula (I) or pharmaceutically acceptable salt thereof

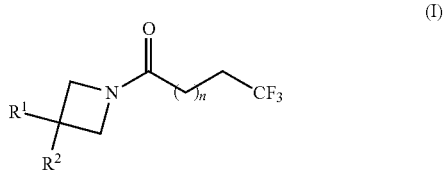

(I)

wherein
n is 1 or 2;
$R^1$ is hydrogen, fluoro, methyl or methoxy; and
$R^2$ is phenyl, pyridyl, $C_{3-6}$ cycloalkyl, piperidin-1-yl or tetrahydropyranyl,
wherein
phenyl and pyridyl are optionally substituted by one to three substituents independently selected from chloro, fluoro, cyano, $C_{1-3}$ alkyl optionally substituted by one or more fluoro, or $C_{1-3}$ alkoxy optionally substituted by one or more fluoro, and
cycloalkyl, piperidin-1-yl and tetrahydropyranyl are optionally substituted by one or two fluoro.

In one embodiment, the compound of the invention is a compound of Formula (I).

When the cycloalkyl, piperidin-1-yl and tetrahydropyranyl group have two fluoro substituents, they may be attached to the same carbon atom.

In one embodiment, n is 1.

In one embodiment, $R^1$ is H.

In one embodiment, $R^2$ is phenyl, pyridyl, $C_{3-6}$ cycloalkyl, piperidin-1-yl or tetrahydropyranyl,
wherein phenyl and pyridyl are substituted by one to three substituents independently selected from chloro, fluoro, cyano, $C_{1-3}$ alkyl optionally substituted by one or more fluoro, or $C_{1-3}$ alkoxy optionally substituted by one or more fluoro,
cycloalkyl is unsubstituted, and
piperidin-1-yl and tetrahydropyranyl is optionally substituted by one or two fluoro each of which may be attached to the same carbon atom.

In one embodiment, $R^2$ is phenyl, pyridyl or $C_{3-6}$ cycloalkyl,
wherein phenyl and pyridyl are substituted by one to three substituents independently selected from chloro, fluoro, cyano, $C_{1-3}$ alkyl optionally substituted by one or more fluoro, or $C_{1-3}$ alkoxy optionally substituted by one or more fluoro, and
cycloalkyl is unsubstituted.

In one embodiment, $R^2$ is phenyl, pyridyl or $C_{3-6}$ cycloalkyl,
wherein phenyl and pyridyl are optionally substituted by one to three substituents independently selected from chloro, fluoro, methyl optionally substituted by one of more fluoro, or methoxy substituted by one of more fluoro, and
cycloalkyl is unsubstituted.

In one embodiment, $R^2$ is phenyl, pyridyl or $C_{3-6}$ cycloalkyl,
wherein phenyl and pyridyl are substituted by one to three substituents independently selected from chloro, fluoro, methyl optionally substituted by one of more fluoro, or methoxy substituted by one of more fluoro, and
cycloalkyl is unsubstituted.

In one embodiment, $R^2$ is phenyl, pyridyl or $C_{3-6}$ cycloalkyl,
wherein phenyl and pyridyl are optionally substituted by one to three substituents independently selected from chloro, fluoro, trifluoromethyl, methoxy or trifluoromethoxy, and
cycloalkyl is unsubstituted.

In one embodiment, particularly when $R^1$ is hydrogen, $R^2$ is phenyl, pyridyl or $C_{3-6}$ cycloalkyl,
wherein phenyl and pyridyl are optionally substituted by one to three substituents independently selected from chloro and fluoro, and
cycloalkyl is unsubstituted.

In one embodiment, particularly when $R^1$ is hydrogen, $R^2$ is phenyl, pyridyl or $C_{3-6}$ cycloalkyl, wherein phenyl and pyridyl are substituted by one to three substituents independently selected from chloro and fluoro, and
cycloalkyl is unsubstituted.

In one embodiment, $R^2$ is pyridyl optionally substituted by any one of the optional substituents defined in any one of the above-mentioned embodiments, or $R^2$ is unsubstituted $C_{3-6}$ cycloalkyl.

In one embodiment, $R^2$ is phenyl or pyridyl optionally substituted by one to three substituents independently selected from chloro, fluoro, cyano, $C_{1-3}$ alkyl optionally substituted by one or more fluoro, or $C_{1-3}$ alkoxy optionally substituted by one or more fluoro.

In one embodiment, $R^2$ is phenyl or pyridyl optionally substituted by one to three substituents independently selected from fluoro, chloro, methyl, methoxy, cyano, trifluoromethyl, trifluoromethoxy, iso-propoxy, —$OCH_2CF_3$.

In one embodiment, $R^2$ is phenyl or pyridyl substituted by one to three substituents independently selected from fluoro, chloro, methyl, methoxy, cyano, trifluoromethyl, trifluoromethoxy, iso-propoxy, —$OCH_2CF_3$.

In another embodiment, $R^2$ is pyridyl optionally substituted by one to three substituents independently selected from fluoro, chloro, methoxy, trifluoromethyl, iso-propoxy, —$OCH_2CF_3$.

In another embodiment, $R^2$ is pyridyl substituted by one to three substituents independently selected from fluoro, chloro, methoxy, cyano, trifluoromethyl, iso-propoxy, —$OCH_2CF_3$. In an embodiment, the pyridyl is substituted by one of these groups only.

In another embodiment, $R^2$ is phenyl optionally substituted by one to three substituents independently selected from fluoro, chloro, methyl, cyano, trifluoromethyl, trifluoromethoxy.

In another embodiment, $R^2$ is phenyl substituted by one to three substituents independently selected from fluoro, chloro, methyl, cyano, trifluoromethyl, trifluoromethoxy.

In one embodiment, $R^1$ is fluoro, methyl or methoxy.

In one embodiment, when $R^1$ is fluoro, methyl or methoxy, $R^2$ is phenyl optionally substituted by one to three substituents independently selected from chloro, fluoro, cyano, $C_{1-3}$ alkyl optionally substituted by one or more fluoro, or $C_{1-3}$ alkoxy optionally substituted by one or more fluoro.

In one embodiment, when $R^1$ is fluoro, methyl or methoxy, $R^2$ is phenyl optionally substituted by one fluoro. In particular, in this embodiment, $R^2$ is phenyl substituted by one fluoro.

In each of the above described embodiments, where it is stated that each group may be optionally substituted or substituted by one to three substituents, each group may be substituted by one or two substituents, only.

In particular, when $R^2$ is pyridyl or phenyl, it is optionally substituted by one or two groups selected from those defined above.

In all of the above described embodiments, it is preferable that $R^2$, when substituted, is substituted by one substituent only.

Furthermore, when $R^2$ is phenyl or pyridyl substituted by two or three groups, those groups are, preferably, independently selected from chloro and fluoro.

Any reference to "pyridyl" is preferably a reference to "2-pyridyl" or "3-pyridyl".

Particular compounds which are useful in the present invention include:
4,4,4-trifluoro-1-[3-(4-fluorophenyl)azetidin-1-yl]butan-1-one;
4,4,4-trifluoro-1-[3-[3-(trifluoromethyl)phenyl]azetidin-1-yl]butan-1-one;
5,5,5-trifluoro-1-[3-(4-fluorophenyl)azetidin-1-yl]pentan-1-one;
1-(3-cyclopropylazetidin-1-yl)-4,4,4-trifluoro-butan-1-one;
1-(3-cyclopentylazetidin-1-yl)-4,4,4-trifluoro-butan-1-one;
1-(3-cyclohexylazetidin-1-yl)-4,4,4-trifluoro-butan-1-one;
4,4,4-trifluoro-1-[3-[4-(trifluoromethyl)-2-pyridyl]azetidin-1-yl]butan-1-one;
4,4,4-trifluoro-1-[3-[5-(trifluoromethyl)-2-pyridyl]azetidin-1-yl]butan-1-one;
4,4,4-trifluoro-1-[3-(5-fluoro-2-pyridyl)azetidin-1-yl]butan-1-one;
1-[3-(3,5-difluoro-2-pyridyl)azetidin-1-yl]-4,4,4-trifluoro-butan-1-one;
1-[3-(4-chloro-2-pyridyl)azetidin-1-yl]-4,4,4-trifluoro-butan-1-one;
4,4,4-trifluoro-1-[3-[2-(trifluoromethyl)-4-pyridyl]azetidin-1-yl]butan-1-one;

1-[3-(4-chlorophenyl)azetidin-1-yl]-4,4,4-trifluoro-butan-1-one;
4,4,4-trifluoro-1-[3-[4-(trifluoromethoxy)phenyl]azetidin-1-yl]butan-1-one;
4,4,4-trifluoro-1-[3-[3-(trifluoromethoxy)phenyl]azetidin-1-yl]butan-1-one;
4,4,4-trifluoro-1-[3-[4-(trifluoromethoxy)phenyl]azetidin-1-yl]butan-1-one;
1-[3-(3-chlorophenyl)azetidin-1-yl]-4,4,4-trifluoro-butan-1-one;
1-[3-(2,4-difluorophenyl)azetidin-1-yl]-4,4,4-trifluoro-butan-1-one;
1-[3-(2,4-difluorophenyl)azetidin-1-yl]-4,4,4-trifluoro-butan-1-one;
1-[3-(2-chloro-4-fluoro-phenyl)azetidin-1-yl]-4,4,4-trifluoro-butan-1-one;
4,4,4-trifluoro-1-[3-[6-(trifluoromethyl)-3-pyridyl]azetidin-1-yl]butan-1-one;
4,4,4-trifluoro-1-[3-(6-methoxy-3-pyridyl)azetidin-1-yl]butan-1-one;
1-[3-(5-chloro-3-pyridyl)azetidin-1-yl]-4,4,4-trifluoro-butan-1-one;
4,4,4-trifluoro-1-[3-[5-(trifluoromethyl)-3-pyridyl]azetidin-1-yl]butan-1-one;
4,4,4-trifluoro-1-[3-[4-fluoro-2-(trifluoromethyl)phenyl]azetidin-1-yl]butan-1-one;
4,4,4-trifluoro-1-[3-(3-pyridyl)azetidin-1-yl]butan-1-one;
1-[3-(3,4-difluorophenyl)azetidin-1-yl]-4,4,4-trifluoro-butan-1-one;
4,4,4-trifluoro-1-[3-(4-fluoro-2-methyl-phenyl)azetidin-1-yl]butan-1-one;
4,4,4-trifluoro-1-[3-(3-fluorophenyl)azetidin-1-yl]butan-1-one;
4,4,4-trifluoro-1-[3-(4-pyridyl)azetidin-1-yl]butan-1-one;
4,4,4-trifluoro-1-[3-(2-fluoro-4-pyridyl)azetidin-1-yl]butan-1-one;
1-[3-(2-chloro-4-pyridyl)azetidin-1-yl]-4,4,4-trifluoro-butan-1-one;
4,4,4-trifluoro-1-[3-(6-fluoro-3-pyridyl)azetidin-1-yl]butan-1-one;
4,4,4-trifluoro-1-[3-(3,4,5-trifluorophenyl)azetidin-1-yl]butan-1-one;
1-[3-(4,4-difluoro-1-piperidyl)azetidin-1-yl]-4,4,4-trifluoro-butan-1-one;
4,4,4-trifluoro-1-[3-(6-isopropoxy-3-pyridyl)azetidin-1-yl]butan-1-one;
4,4,4-trifluoro-1-[3-[6-(2,2,2-trifluoroethoxy)-3-pyridyl]azetidin-1-yl]butan-1-one;
4,4,4-trifluoro-1-(3-(tetrahydro-2H-pyran-4-yl)azetidin-1-yl)butan-1-one;
1-(3-(4,4-difluorocyclohexyl)azetidin-1-yl)-4,4,4-trifluorobutan-1-one;
4,4,4-trifluoro-1-(3-(piperidin-1-yl)azetidin-1-yl)butan-1-one;
4,4,4-trifluoro-1-(3-(4-fluorophenyl)-3-methoxyazetidin-1-yl)butan-1-one;
4,4,4-trifluoro-1-(3-(4-fluorophenyl)-3-methylazetidin-1-yl)butan-1-one;
4-(1-(4,4,4-trifluorobutanoyl)azetidin-3-yl)benzonitrile; and
4,4,4-trifluoro-1-(3-fluoro-3-(4-fluorophenyl)azetidin-1-yl)butan-1-one.

Terms and Definitions

As used herein, the term "$C_{3-6}$ cycloalkyl" refers to a monocyclic saturated ring containing three to six carbon atoms. Therefore, the term includes cyclopropyl, cyclobutyl, cyclopentyl and cyclohexyl.

As used herein, the term "cyano" refers to —CN.

As used herein, the term "$C_{1-3}$ alkyl" refers to a straight or branched chain alkyl group having one to three carbon atoms. Therefore, the term "$C_{1-3}$ alkyl" includes methyl, ethyl, n-propyl and iso-propyl.

As used herein, the term "$C_{1-3}$ alkoxy" refers to a straight or branched chain alkoxy group having one to three carbon atoms. Therefore, the term "$C_{1-3}$ alkoxy" includes methoxy, ethoxy, n-propoxy and iso-propoxy.

The term "compounds of the invention" as used herein means a compound of Formula (I) or a pharmaceutically acceptable salt thereof. The term "a compound of the invention" means any one of the compounds of the invention as defined above.

Furthermore, it will be understood that phrases such as "a compound of Formula (I) or a pharmaceutically acceptable salt thereof" or "compounds of the invention" are intended to encompass the compound of Formula (I), a pharmaceutically acceptable salt or solvate of the compound of Formula (I), or any pharmaceutically acceptable combination of these. Thus by way of non-limiting example used here for illustrative purpose, "a compound of Formula (I) or a pharmaceutically acceptable salt thereof" encompasses a pharmaceutically acceptable salt of a compound of Formula (I) which is present as a solvate, and this phrase also encompasses a mixture of a compound of Formula (I) and a pharmaceutically acceptable salt of a compound of Formula (I).

It is to be understood that references herein to a compound of Formula (I) or a pharmaceutically acceptable salt thereof includes a compound of Formula (I) as a free base or as a pharmaceutically acceptable salt thereof. Thus, in one embodiment, the invention is directed to a compound of Formula (I). In another embodiment, the invention may be directed to a pharmaceutically acceptable salt of a compound of Formula (I).

The term "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: Wiley-VCH/VHCA, 2011 (see http://www.wiley.com/WileyCDA/WileyTitle/productCd-3906390519.html).

Suitable pharmaceutically acceptable salts can include acid addition salts. Such salts can be formed by reaction with the appropriate acid, optionally in a suitable solvent such as an organic solvent, to give the salt which can be isolated by crystallisation and filtration.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbitu rate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder.

An appropriate "therapeutically effective amount" will depend upon a number of factors including, for example, the age and weight of the subject, the precise condition requiring treatment and its severity, the nature of the formulation, and the route of administration, and will ultimately be at the discretion of the attendant physician.

Compound Preparation

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention can be prepared according to the experimental procedures disclosed in the Examples section.

The general procedures used to synthesise the compounds of Formula (I) are described in reaction Schemes 1 to 11 below and are illustrated in the examples.

Preparation of Compounds of Formula (I)

Compounds of Formula (I) wherein $R^1$ and $R^2$ are as defined hereinbefore may be prepared according to Scheme 1 by BOC deprotection of amino compounds of Formula (III) using hydrogen chloride or trifluoroacetic acid followed by coupling of the corresponding TFA or HCl salt of Formula (II) with 4,4,4-trifluorobutanoic acid or 4,4,4-trifluorobutanoylbenzotriazole or 5,5,5-trifluoropentanoylbenzotriazole.

Scheme 1

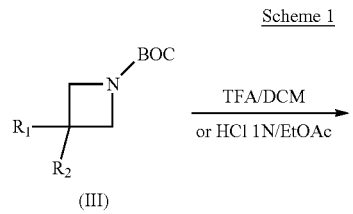

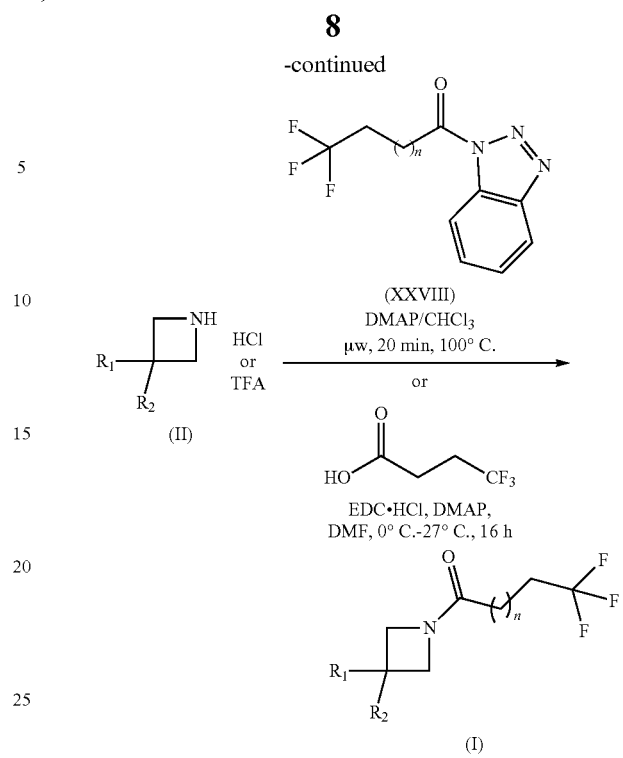

Alternatively, compounds with Formula (I) can be prepared by reaction of the corresponding commercially available free amino compounds of Formula (II) with 4,4,4-trifluorobutanoylbenzotriazole.

Compounds of Formula (IV) which are alkoxypyridine compounds of Formula (I) wherein $R^1$ is H and $R^2$ is pyridyl substituted by $C_{1-3}$ alkoxy optionally substituted by one or more fluoro may be prepared according to Scheme 2 by reaction of the corresponding commercially available alcohols with fluoropyridine compound of Formula (V).

Scheme 2

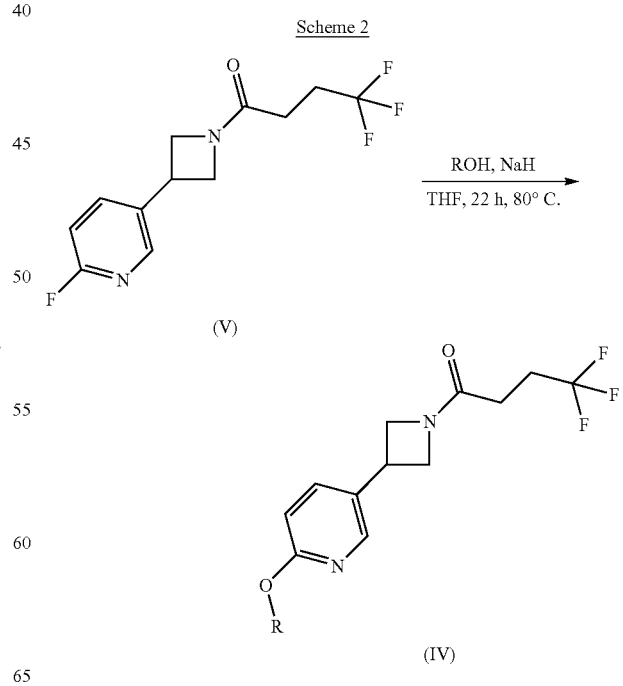

Compound of Formula (VI) which is a 3-fluoroazetidine compound of Formula (I) wherein $R^1$ is F and $R^2$ is 4-fluorophenyl can be prepared according to Scheme 3 by deoxofluorination reaction using N,N-diethylaminosulfur trifluoride with corresponding hydroxyazetidine compound of Formula (VII).

Scheme 3

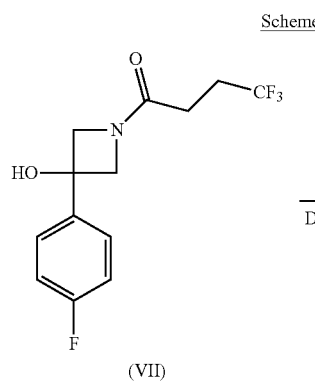

(VII)

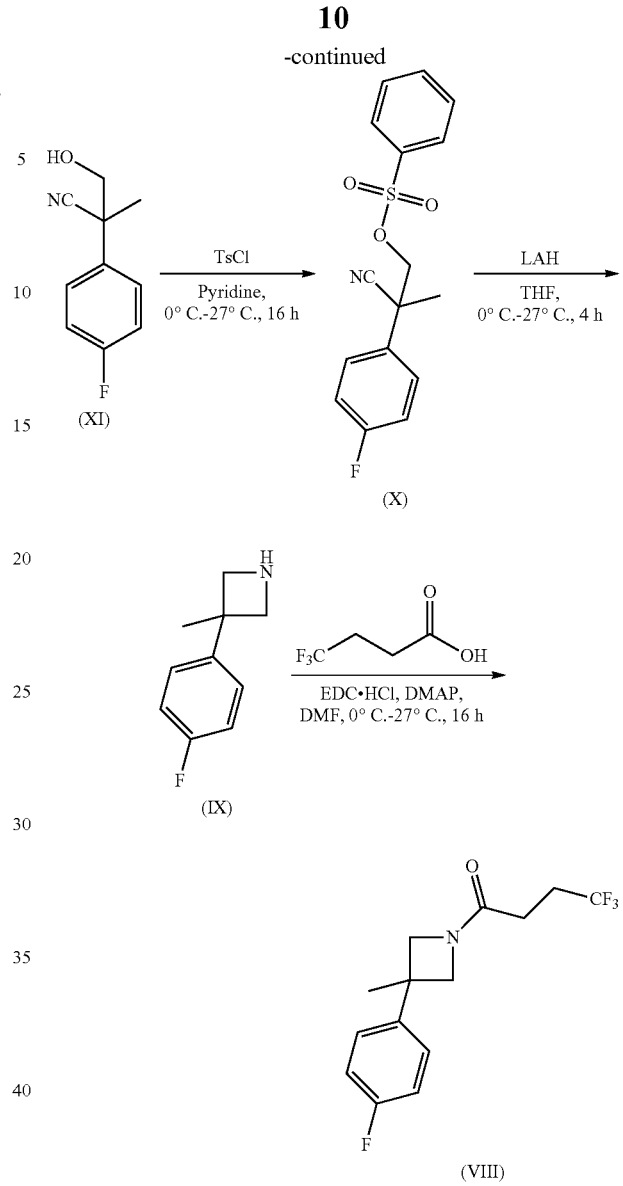

Compound of Formula (VIII) which is a 4-methylazetidine compound of Formula (I) wherein $R^1$ is methyl and $R^2$ is 4-fluorophenyl can be prepared according to Scheme 4 by coupling compound of Formula (IX) with 4,4,4-trifluorobutanoic acid. Compound of Formula (IX) may be prepared by cyclisation of cyano compound of Formula (X) using lithium aluminium hydride. Compound of Formula (X) can be prepared starting from 2-(4-fluorophenyl)acetonitrile that is reacting with iodomethane and potassium tert-butoxide followed by a reaction with paraformaldehyde to give the intermediate alcohol of Formula (XI) which can finally react with p-toluenesulfonyl chloride in pyridine to give compound of Formula (X).

Scheme 4

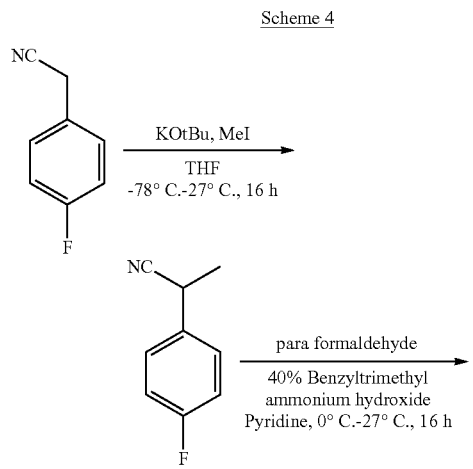

Preparation of Intermediates

Azetidine intermediates of Formula (XII) wherein $R^1$ is H and $R^2$ is 4- or 5-trifluoropyridin-2-yl can be prepared according to Scheme 5 by a CH-activation reaction of an appropriate pyridine with sulfinate intermediate of Formula (XIV) followed by a deprotection step of compounds of Formula (XIII) with triethylsilane. The sulfonate intermediate of Formula (XIV) may be prepared by the cleavage of the pyridine group of compound of Formula (XV) with sodium ethanethiolate. The sulfone compound of Formula (XV) can be obtained via the homolysis of ester compound of Formula (XVII) into thiopyridyl substrate (XVI) followed by an oxidation with ruthenium chloride. The compound of Formula (XVII) may be obtained by reaction of carboxylic acid of Formula (XIX) with oxalyl chloride followed by the formation of the Barton ester intermediate using 2-mercaptopyridine N-oxide. The compound of Formula (XIX) can be obtained by a protection step of the corresponding amino compound with benzylchloroformate.

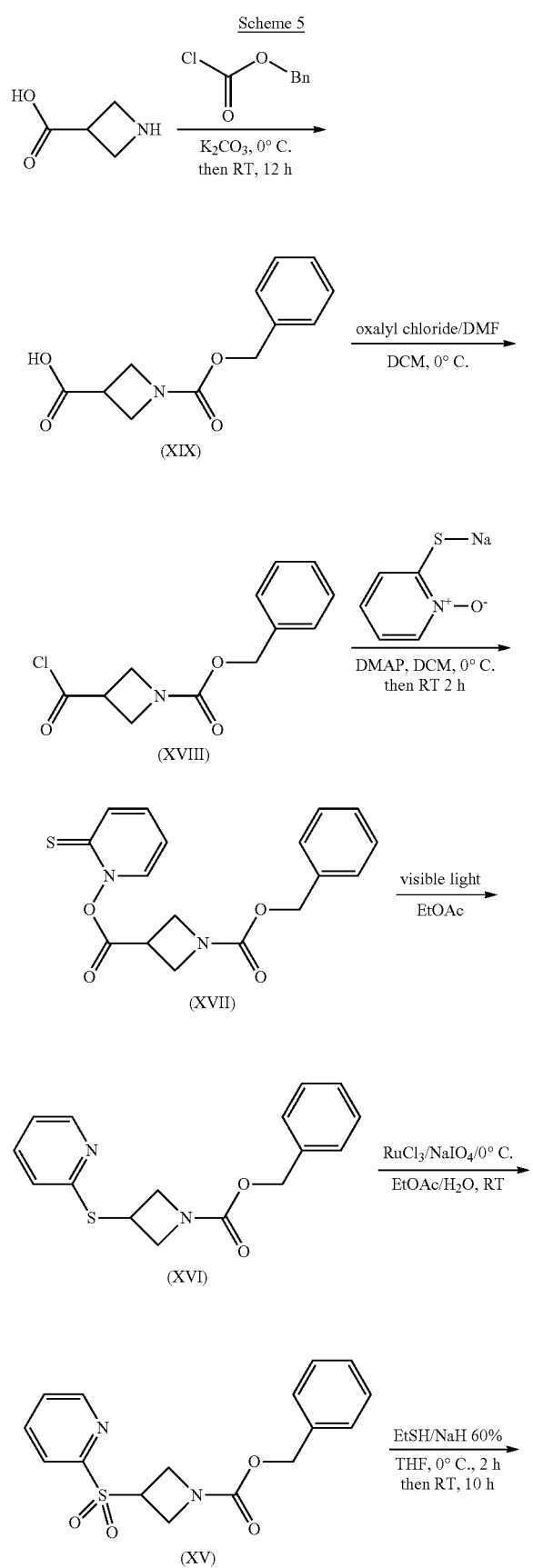

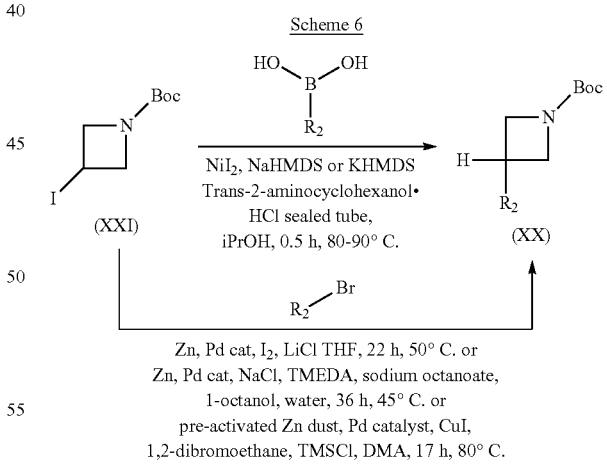

Intermediates of Formula (XX) wherein $R^2$ is as defined hereinbefore and $R^1$ is H may be prepared according to Scheme 6 by cross-coupling reaction of commercially available iodoazetidine compound of Formula (XXI) with appropriate boronic acids using nickel(II) iodide as catalyst, sodium or potassium bis(trimethylsilyl)amide and trans-2-aminocyclohexanol. Alternatively, intermediates of Formula (XX) may be prepared by Negishi coupling reaction of commercially available iodoazetidine compound of Formula (XXI) with appropriate halogenated compounds.

Heterocycloalkyl or difluorocycloalkyl intermediates of Formula (XXII) wherein $R^1$ is H and $R^2$ is as defined hereinbefore for a compound of Formula (I) can be prepared according to Scheme 7 by a cross-coupling reaction of iodoazetidine compound of Formula (XXI) with appropriate pinacolborane compound using nickel(II) chloride followed by a reduction step of intermediate of Formula (XXIII) in the presence of dihydrogen and palladium on activated charcoal.

Scheme 7

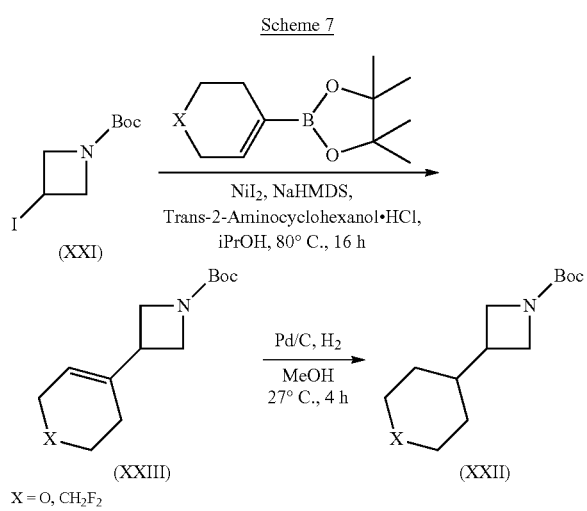

X = O, CH₂F₂

Heterocycloalkyl intermediate of Formula (XXIV) wherein $R^1$ is H and $R^2$ is a 4,4-difluoropiperidine group can be prepared according to Scheme 8 by a substitution reaction of iodoazetidine compound of Formula (XXI) with commercially available 4,4-difluoropiperidine in the presence of potassium carbonate.

Scheme 8

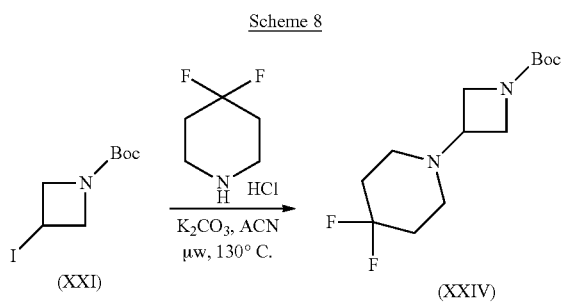

Heterocycloalkyl intermediate of Formula (XXV) wherein $R^1$ is H and $R^2$ is a piperidine can be prepared according to Scheme 9 by a reductive amination reaction of commercially available N-Boc protected azetidin-4-one and piperidine in the presence of formic acid and sodium triacetoxyborohydride.

Scheme 9

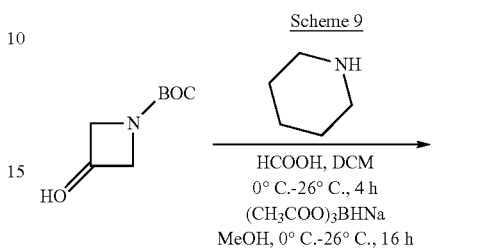

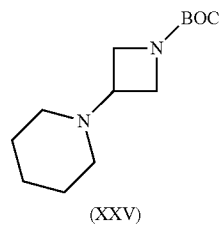

Intermediate of Formula (XXVI) wherein $R^1$ is OCH₃ and $R^2$ is a 4-fluorophenyl can be prepared according to Scheme 10 from an alkylation reaction of the corresponding alcohol of Formula (XXVII) using sodium hydride and iodomethane. Compound of Formula (XXVII) may be prepared from commercially available N-Boc protected azetidin-3-one and Grignard reagent 4-fluorophenylorganomagnesium bromide. Alternatively compound of Formula (XXVII) may be prepared by an addition reaction of organolithium derivative prepared using 4-fluorobromophenyl and butyllithium in THF and the commercially available N-Boc protected azetidin-3-one.

Scheme 10

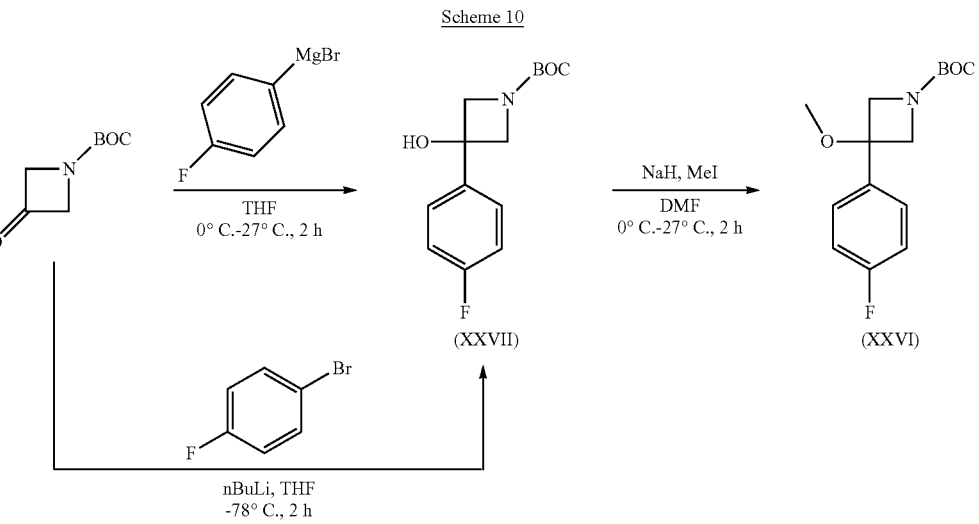

Intermediate of Formula (XXVIII) wherein n=1 or 2 may be prepared according to scheme 11 by a reaction between benzotriazole and 4,4,4-trifluorobutanoic acid or 5,5,5-trifluoropentanoic acid in the presence of thionyl chloride.

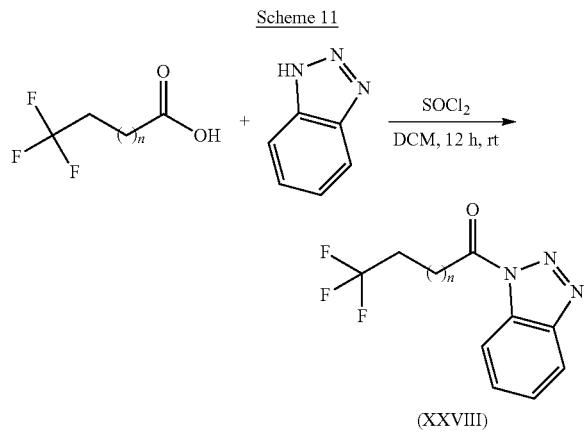

Scheme 11

(XXVIII)

Methods of Use

In one aspect, the invention relates to a compound of Formula (I), or a pharmaceutically acceptable salt thereof, for use in therapy.

In one aspect, the invention relates to a compound of Formula (I), or a pharmaceutically acceptable salt thereof, for use in the treatment of a mycobacterial infection. A mycobacterial infection is one caused by infection with a *Mycobacterium*.

The *Mycobacterium* may be a member of one of the following groups of *Mycobacterium*: *Mycobacterium tuberculosis* complex (MTC), *Mycobacterium avium* complex (MAC), *Mycobacterium gordonae* clade, *Mycobacterium kansasii* clade, *Mycobacterium chelonae* clade, *Mycobacterium fortuitum* clade, *Mycobacterium parafortuitum* clade or *Mycobacterium vaccae* clade. The *Mycobacterium* may also be *Mycobacterium ulcerans* or *Mycobacterium leprae*.

Members of *Mycobacterium tuberculosis complex* (MTC) include *Mycobacterium tuberculosis*, *Mycobacterium africanum*, *Mycobacterium bovis*, *Mycobacterium bovis* BCG, *Mycobacterium canetti*, *Mycobacterium caprae*, *Mycobacterium microti* and *Mycobacterium pinnipedii*. These mycobacteria are causative agents of human and animal tuberculosis. *Mycobacterium tuberculosis* is the major cause of human tuberculosis.

In one embodiment, the *Mycobacterium* is a member of the *Mycobacterium tuberculosis* complex (MTC).

In one embodiment, the infection is a *Mycobacterium tuberculosis* infection. In other words, the mycobacterial infection is caused by infection with *Mycobacterium tuberculosis*.

In one embodiment, the *Mycobacterium tuberculosis* is multidrug-resistant. In another embodiment the *Mycobacterium tuberculosis* is resistant to ethionamide.

Members of *Mycobacterium avium complex* (MAC) include *Mycobacterium avium*, *Mycobacterium avium paratuberculosis*, *Mycobacterium avium silaticum*, *Mycobacterium avium hominissuis*, *Mycobacterium columbiense* and *Mycobacterium indicus pranii*.

Members of *Mycobacterium gordonae clade* include *Mycobacterium asiaticum* and *Mycobacterium gordonae*.

Members of *Mycobacterium kansasii clade* include *Mycobacterium gastri* and *Mycobacterium kansasii*.

Members of *Mycobacterium chelonae clade* include *Mycobacterium abscessus*, *Mycobacterium bolletii* and *Mycobacterium chelonae*.

Members of *Mycobacterium fortuitum clade* include *Mycobacterium boenickei*, *Mycobacterium brisbanense*, *Mycobacterium cosmeticum*, *Mycobacterium fortuitum*, *Mycobacterium fortuitum* subspecies *acetamidolyticum*, *Mycobacterium houstonense*, *Mycobacterium mageritense*, *Mycobacterium neworleansense*, *Mycobacterium peregrinum*, *Mycobacterium porcinum*, *Mycobacterium senegalense* and *Mycobacterium septicum*.

Members of *Mycobacterium parafortuitum clade* include *Mycobacterium austroafricanum*, *Mycobacterium diernhoferi*, *Mycobacterium frederiksbergense*, *Mycobacterium hodleri*, *Mycobacterium neoaurum* and *Mycobacterium parafortuitum*.

Therefore, the mycobacterial infection may be caused by infection with a *Mycobacterium* selected from the following: *Mycobacterium tuberculosis*, *Mycobacterium africanum*, *Mycobacterium bovis*, *Mycobacterium bovis* BCG, *Mycobacterium canetti*, *Mycobacterium caprae*, *Mycobacterium microti*, *Mycobacterium pinnipedii*, *Mycobacterium avium*, *Mycobacterium avium paratuberculosis*, *Mycobacterium avium silaticum*, *Mycobacterium avium hominissuis*, *Mycobacterium columbiense*, *Mycobacterium indicus pranii*, *Mycobacterium asiaticum*, *Mycobacterium gordonae*, *Mycobacterium gastri*, *Mycobacterium kansasii*, *Mycobacterium abscessus*, *Mycobacterium bolletii*, *Mycobacterium chelonae*, include *Mycobacterium boenickei*, *Mycobacterium brisbanense*, *Mycobacterium cosmeticum*, *Mycobacterium fortuitum*, *Mycobacterium fortuitum* subspecies *acetamidolyticum*, *Mycobacterium houstonense*, *Mycobacterium mageritense*, *Mycobacterium neworleansense*, *Mycobacterium peregrinum*, *Mycobacterium porcinum*, *Mycobacterium senegalense*, *Mycobacterium septicum*, *Mycobacterium austroafricanum*, *Mycobacterium diernhoferi*, *Mycobacterium frederiksbergense*, *Mycobacterium hodleri*, *Mycobacterium neoaurum*, *Mycobacterium parafortuitum*, *Mycobacterium ulcerans* and *Mycobacterium leprae*.

In another aspect, the invention relates to a compound of Formula (I), or a pharmaceutically acceptable salt thereof, for use in the treatment of a disease caused by infection with a *Mycobacterium*, where the *Mycobacterium* is selected from those hereinbefore described.

Diseases caused by infection with a *Mycobacterium* include, but are not limited to, tuberculosis (e.g. from *Mycobacterium tuberculosis*), leprosy (e.g. from *Mycobacterium leprae*), Johne's disease (e.g. from *Mycobacterium avium* subspecies paratuberculosis), Buruli or Bairnsdale ulcer (e.g. from *Mycobacterium ulceran*), Crohn's disease (e.g. from *Mycobacterium avium* subspecies *paratuberculosis*), pulmonary disease or pulmonary infection, pneumonia, bursa, synovial, tendon sheaths, localized abscess, lymphadenitis, skin and soft tissue infections, Lady Windermere syndrome (e.g. from *Mycobacterium avium* complex (MAC)), MAC lung disease, disseminated *Mycobacterium avium* complex (DMAC), disseminated *Mycobacterium avium intracellulare* complex (DMAIC), hot-tub lung (e.g. from *Mycobacterium avium* complex), MAC mastitis, MAC pyomyositis, or granuloma disease.

In one embodiment, the disease is tuberculosis. Thus, one aspect of the invention relates to a compound of Formula (I), or a pharmaceutically acceptable salt thereof, for use in the treatment of tuberculosis.

In one embodiment, the invention relates to a method of treatment of a mycobacterial infection in a mammal in need thereof, said treatment comprising administering to said mammal a therapeutically effective amount of a compound of Formula (I), or pharmaceutically acceptable salt thereof. As described herein, a mycobacterial infection is one caused by infection with a *Mycobacterium*. The *Mycobacterium* is as hereinbefore described.

In one embodiment, the mycobacterial infection is a *Mycobacterium tuberculosis* infection.

In another embodiment, the invention relates to a method of treatment of a disease caused by infection with a *Mycobacterium* in a mammal in need thereof, said treatment comprising administering to said mammal a therapeutically effective amount of a compound of Formula (I), or a pharmaceutically acceptable salt thereof.

In one embodiment, the disease is tuberculosis. Therefore, also described herein is a method of treatment of tuberculosis in a mammal in need thereof, said treatment comprising administering to said mammal a therapeutically effective amount of a compound of Formula (I), or a pharmaceutically acceptable salt thereof.

In one embodiment, the mammal is a human.

It will be appreciated by those skilled in the art that references herein to treatment refer to the treatment of established conditions. However, compounds of the invention may, depending on the condition, also be useful in the prevention of certain diseases. Thus, in one embodiment, there is provided the treatment or prevention of a disease such as TB. In another embodiment, there is provided the treatment of a disease such as TB. In a further embodiment, there is provided the prevention of a disease such as TB.

In another embodiment, the invention relates to use of a compound of Formula (I), or a pharmaceutically acceptable salt thereof, in the manufacture of a medicament for use in the treatment of a mycobacterial infection or in the treatment of a disease caused by infection with a *Mycobacterium*.

Also described herein is the use of a compound of Formula (I), or a pharmaceutically acceptable salt thereof, in the manufacture of a medicament for use in the treatment of tuberculosis.

In one embodiment, a compound of Formula (I) or pharmaceutically acceptable salt thereof, for use in the treatment of TB, is co-administered with a thioamide. In a further embodiment, the thioamide is ethionamide. In an alternative embodiment, the thioamide is prothionamide.

Consequently, in one embodiment there is provided a pharmaceutical composition for use in the treatment of TB, wherein said composition comprises (a) a compound of Formula (I); (b) a thioamide, for example ethionamide or prothionamide; and optionally (c) a pharmaceutically acceptable excipient.

In another embodiment, the invention relates to a method of treatment of a mycobacterial infection in a mammal in need thereof, said treatment comprising administering to said mammal a therapeutically effective amount of a compound of Formula (I), or pharmaceutically acceptable salt thereof, in combination with a thioamide, wherein said thioamide may be ethionamide. In an alternative embodiment, the thioamide is prothionamide. As described herein, a mycobacterial infection is one caused by infection with a *Mycobacterium*. The *Mycobacterium* is as hereinbefore described.

In one embodiment, the mycobacterial infection is a *Mycobacterium tuberculosis* infection.

In another embodiment, the invention relates to a method of treatment of a disease caused by infection with a *Mycobacterium* in a mammal in need thereof, said treatment comprising administering to said mammal a therapeutically effective amount of a compound of Formula (I), or a pharmaceutically acceptable salt thereof, in combination with a thioamide, wherein said thioamide may be ethionamide. In an alternative embodiment, the thioamide is prothionamide.

In one embodiment, the disease is tuberculosis. Therefore, also described herein is a method of treatment of tuberculosis in a mammal in need thereof, said treatment comprising administering to said mammal a therapeutically effective amount of a compound of Formula (I), or a pharmaceutically acceptable salt thereof, in combination with a thioamide, wherein said thioamide may be ethionamide. In an alternative embodiment, the thioamide is prothionamide.

In another embodiment, the invention relates to use of a compound of Formula (I), or a pharmaceutically acceptable salt thereof, in combination with a thioamide (for example, ethionamide), in the manufacture of a medicament for use in the treatment of a mycobacterial infection or in the treatment of a disease caused by infection with a *Mycobacterium*. In an alternative embodiment, the thioamide is prothionamide.

Also described herein is the use of a compound of Formula (I), or a pharmaceutically acceptable salt thereof, in combination with a thioamide (for example, ethioamide) in the manufacture of a medicament for use in the treatment of tuberculosis. In an alternative embodiment, the thioamide is prothionamide.

Pharmaceutical Compositions

The compounds of Formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of Formula (I), or a pharmaceutically acceptable salt thereof, and a pharmaceutically acceptable excipient.

Pharmaceutical compositions may be administered by any appropriate route, for example by the oral (including buccal or sublingual), rectal, inhaled, intranasal, topical (including buccal, sublingual or transdermal) or parenteral (including subcutaneous, intramuscular, intravenous or intradermal) route. In particular, pharmaceutical compositions of the invention may be administered by oral or intravenous route.

Suitable pharmaceutically acceptable excipients include the following types of excipients: carriers, diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants and buffering agents.

Suitable methods for formulating compounds of the invention will be familiar to those skilled in the art, which are described in Remington: The Science and Practice of Pharmacy, $21^{st}$ Edition 2006.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

When the compounds of the invention or pharmaceutically acceptable salts thereof are used in the treatment of tuberculosis, they may be employed alone or in combination with a further therapeutic agent, such as a further anti-mycobacterial agent, for example an anti-tuberculosis agent and/or antiviral agent, including antiretroviral agents.

For example, the present invention relates to compounds of Formula (I) or pharmaceutically acceptable salts thereof, in combination with a further anti-tuberculosis agent. In an embodiment, the combination comprises two, three, four, five, six or seven additional anti-tuberculosis agents. For example, in the treatment of multidrug-resistant tuberculosis, it is common that combinations of four or more drugs are administered to patients. For example, in the treatment of drug-sensitive tuberculosis, it is common that combinations of three or four drugs are administered to patients.

The further anti-tuberculosis agent is an agent in development, approved or recommended for the treatment of tuberculosis and may be selected from isoniazid, rifampin, pyrazinamide, ethambutol, moxifloxacin, rifapentine, clofazimine, ethionamide, prothionamide, isoxyl, thiacetazone, rifabutin, a diarylquinoline such as bedaquiline (TMC207) or TBAJ-587, nitroimidazo-oxazine PA-824, delamanid (OPC-67683), an oxazolidinone such as linezolid, tedizolid, radezolid, sutezolid (PNU-100480), posizolid (AZD-5847) or TBI-223, EMB analogue SQ109, OPC-167832, GSK3036656 (also known as GSK070), GSK2556286, GSK3211830, a benzothiazinone such as BTZ043 or PBTZ169, an azaindole such as TBA-7371, a dinitrobenzamide, or a beta-lactam such as meropenem, faropenem, ertapenem, tebipenem or beta-lactam combinations such as AUGMENTIN (amoxicillin-clavulanate).

In an embodiment, the anti-tuberculosis agent may be selected from isoniazid, rifampin, pyrazinamide, ethambutol, moxifloxacin, rifapentine, clofazimine, ethionamide, prothionamide, isoxyl, thiazetazone, bedaquiline (TMC207), nitroimidazo-oxazine PA-824, delamanid (OPC-67683), an oxazolidinone such as linezolid, tedizolid, radezolid, sutezolid (PNU-100480), or posizolid (AZD-5847), EMB analogue SQ109, OPC-167832, GSK3036656A (also known as GSK070), GSK2556286, GSK3211830 and a benzothiazinone or a dinitrobenzamide.

A combination according to the present invention may further comprise an antiviral agent, including an antiretroviral agents.

Such antiretroviral agents may be selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir and darunavir.

A compound of the invention (i.e. a compound of Formula (I) or pharmaceutically acceptable salt thereof) may be used in combination with an anti-tuberculosis agent that is activatable via the EthA pathway. A person skilled in the art is able to determine if a particular compound is activatable via the EthA pathway, for example, by applying the method described in the following publication: "Activation of the prodrug ethionamide is regulated by mycobacteria" A. R. Baulard et al., Journal of Biological Chemistry, 2000, pages 28326-28331.

More particularly, the anti-tuberculosis agent may be chosen from the thioamide family, such as ethionamide, prothionamide, isoxyl and thiazetazone.

In one embodiment, a compound of the invention (i.e. a compound of Formula (I) or pharmaceutically acceptable salt thereof) is used in combination with ethionamide. In this embodiment, the compounds of the invention (i.e. a compound of Formula (I) or a pharmaceutically acceptable salt thereof) have shown to potentiate the activity of ethionamide.

The combinations may conveniently be presented for use in the form of a pharmaceutical composition or formulation.

Therefore, also contemplated herein is a pharmaceutical composition comprising (a) a compound of the invention (i.e. a compound of Formula (I) or pharmaceutically acceptable salt thereof), as herein described, together with (b) one or more pharmaceutically acceptable carriers as herein described, and (c) at least one other anti-tuberculosis drug and (d) optionally an antiviral agent including antiretroviral agents.

A compound of the invention (i.e. a compound of Formula (I) or pharmaceutically acceptable salt thereof) and further therapeutic agent may be administered together or separately and, when administered separately, this may occur separately or sequentially in any order (by the same or by different routes of administration). The amount of a compound of the invention (i.e. a compound of Formula (I) or pharmaceutically acceptable salt thereof) and the further therapeutically active agent(s) and the relative timings of administration will be selected in order to achieve the desired combined therapeutic effect.

EXAMPLES

The invention will now be illustrated by way of the following non-limiting examples. While particular embodiments of the invention are described below a skilled person will appreciate that various changes and modifications can be made. References to preparations carried out in a similar manner to, or by the general method of, other preparations, may encompass variations in routine parameters such as time, temperature, workup conditions, minor changes in reagents amounts, etc.

Abbreviations

The following list provides definitions of certain abbreviations and symbols as used herein. It will be appreciated that the list is not exhaustive, but the meaning of those abbreviations and symbols not herein below defined will be readily apparent to those skilled in the art. In describing the invention, chemical elements are identified in accordance with the Periodic Table of the Elements.
anh Anhydrous
aq. Aqueous
$CDCl_3$ Deuterated chlorofom
$CD_2Cl_2$ Deuterated dichloromethane
CyHex Cyclohexane
DCM Dichloromethane
DIPEA Diisoproylethylamine
DMA Dimethylacetamide
DMAP 4-Dimethylaminopyridine
DMF Dimethylformamide
DMSO-$d_6$ Deuterated dimethylsulfoxide
EDC.HCl N-(3-Dimethylaminopropyl)-N'-ethylcarbodiimidehydrochloride
Eq Equivalents
EtOAc Ethyl acetate
HBTU N,N,N',N'-Tetramethyl-O-(1H-benzotriazol-1-yl) uronium hexafluorophosphate
HPLC High Performance Liquid Chromatography
Int. Intermediate
LC Liquid chromatography
LAH Lithium aluminium hydride
M Molar
MeOH Methanol
EtOH Ethanol
MS Mass spectroscopy
min Minutes
N Normal
NaH Sodium hydride
NMR Nuclear Magnetic Resonance
p-TsOH.$H_2O$ p-Toluenesulfonic acid monohydrate quant. Quantitative
rt Room temperature
TFA Trifluoroacetic acid
TEA Triethylamine
THF Tetrahydrofuran
TLC Thin layer chromatography
TMEDA Tetramethylethylenediamine
TMSCI Trimethylsilyl chloride
UPLC Ultra Performance Liquid Chromatography Proton nuclear magnetic resonance (1H NMR) spectra were recorded, and chemical shifts are reported in parts per million (δ) downfield from the internal standard tetramethylsilane (TMS). Abbreviations for NMR data are as follows: s=singlet, d=doublet, t=triplet, q=quartet, m=multiplet, app=apparent, br=broad. Mass spectra were obtained using electrospray (ES) ionization techniques. All temperatures are reported in degrees centigrade.

In certain of the following Intermediates and Examples, starting materials are identified by reference to other Intermediate or Example numbers. This does not signify that the actual material from any particular Intermediate or Example was necessarily used in a subsequent step exemplified herein, but is used as a short-hand means of denoting the relevant compound name.

Intermediates

Intermediate 1:
1-(benzotriazol-1-yl)-4,4,4-trifluoro-butan-1-one

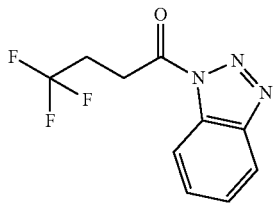 [SMILES: O=C(CCC(F)(F)F)n1nnc2ccccc21]

Thionyl chloride (SIGMA-ALDRICH, 6.74 mL, 93 mmol) and 1H-benzotriazole (ALFA-AESAR, 31.2 g, 262 mmol) in DCM (150 mL) were added dropwise to a solution of 4,4,4-trifluorobutanoic acid (FLUOROCHEM, 12 g, 85 mmol) in DCM (150 mL). The reaction mixture was stirred at rt 12 h. The precipitate was filtered off and the filtrate was dried in vacuo to yield title compound (19.6 g, 94%) as an off-white solid. $^1$H NMR (300 MHz, CD$_2$Cl$_2$) δ ppm: 8.28 (d, J=8.3 Hz, 1H), 8.15 (d, J=8.4 Hz, 1H), 7.75-7.69 (m, 1H), 7.60-7.54 (m, 1H), 3.77 (t, J=7.8 Hz, 2H), 2.91-2.73 (m, 2H). [ES+MS] m/z 244 (MH$^+$).

Intermediate 2:
1-(benzotriazol-1-yl)-5,5,5-trifluoro-pentan-1-one

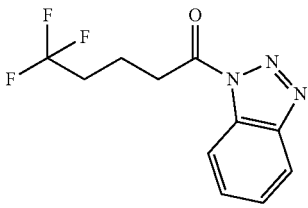 [SMILES: O=C(CCCC(F)(F)F)n1nnc2ccccc21]

Intermediate 2 was prepared using analogous method to that described for Intermediate 1 but replacing 4,4,4-trifluorobutanoic acid with 5,5,5-trifluoropentanoic acid (APOLLO, 1.82 ml, 15.05 mmol). $^1$H NMR (300 MHz, CD$_2$Cl$_2$) δ ppm: 8.30-8.26 (m, 1H), 8.15-8.11 (m, 1H), 7.72-7.66 (m, 1H), 7.57-7.51 (m, 1H), 3.55 (t, J=7.2 Hz, 2H), 2.27-2.44 (m, 2H), 2.13-2.24 (m, 2H).

Intermediate 3:
1-benzyloxycarbonylazetidine-3-carboxylic Acid

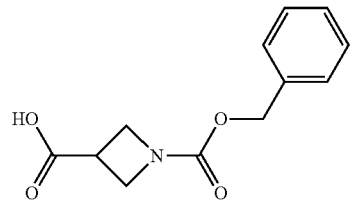 [SMILES: O=C(O)C1CN(C(=O)OCc2ccccc2)C1]

Benzylchloroformate (ALFA-AESAR, 7.93 mL, 55.5 mmol) was added dropwise to a solution of azetidine-3-carboxylic acid (FLUOROCHEM, 4.32 g, 42.7 mmol) and K$_2$CO$_3$ (SIGMA-ALDRICH, 13.6 g, 98.3 mmol) in H$_2$O (50 mL) at 0° C. The reaction was allowed to warm to rt and stirred overnight. The reaction was washed with EtOAc (50 mL) and partitioned. Then the aq. phase was acidified with HCl (1N) until pH=2 and extracted with EtOAc (×2), dried, and concentrated to afford title compound (9.2 g, 91%). $^1$H NMR (300 MHz, CD$_2$Cl$_2$) δ ppm: 10.03 (s, 1H), 7.43-7.27 (m, 5H), 5.12 (s, 2H), 4.31-4.15 (m, 4H), 3.51-3.41 (m, 1H). [ES+MS] m/z 236 (MH$^+$).

Intermediate 4: 1-benzyl
03-(2-thioxo-1-pyridyl)azetidine-1,3-dicarboxylate

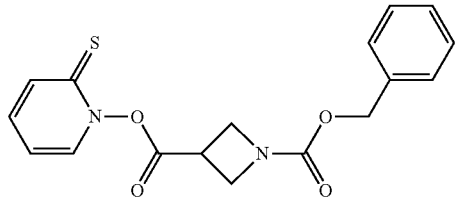 [SMILES: O=C(On1ccccc1=S)C1CN(C(=O)OCc2ccccc2)C1]

Intermediate 3 (5.25 g, 22.3 mmol) was dissolved in DCM (60 mL) at 0° C. DMF (0.17 mL, 2.2 mmol) was added followed by slow addition of oxalyl chloride (ACROS, 2.9 mL, 33.4 mmol) under a stream of argon. The reaction was cooled at 0° C., wrapped in aluminum foil, and shielded from light. DCM (60 mL) was added and the reaction mixture was cooled down to 0° C. DMAP (SIGMA-ALDRICH, 272 mg, 2.2 mmol) was added followed by portionwise addition of 2-mercaptopyridine N-oxide sodium salt (SIGMA-ALDRICH, 5 g, 33.4 mmol). The reaction was allowed to warm to rt and stirred for 2 h. Upon completion of the reaction, the reaction flask was cooled to 0° C. and water (60 mL) was added. The layers were separated (in a separatory funnel that was wrapped in aluminum foil) and the organics were filtered through a pad of Celite while washing with DCM (using a fritted funnel and round bottom flask that were covered with aluminum foil). The organics were concentrated under reduced pressure in a water bath no higher than 25° C. while shielded from light (the bath was covered aluminum foil). The flask was wrapped in aluminum foil and placed under high vacuum to remove any residual DCM to give the title compound which was used in the next step without purification. [ES+MS] m/z 345 (MH$^+$).

Intermediate 5: Benzyl 3-(2-pyridylsulfanyl)azetidine-1-carboxylate

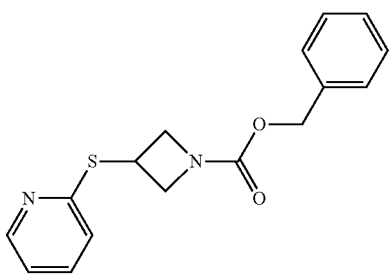 [SMILES: O=C(OCc1ccccc1)N1CC(Sc2ccccn2)C1]

Intermediate 4 (7.7 g, 22.3 mmol) was dissolved in EtOAc (60 mL) and the flask was fitted with a reflux condenser. The reaction was irradiated with a 400 W halogen lamp until consumption of the Barton ester (1 h) (EtOAc usually refluxed after 20 min of irradiation and the Barton esters usually appeared as a yellow spot without UV visualization on TLC). Upon completion of the reaction, water (60 mL) was added and extracted with EtOAc (×2), dried and concentrated. The residue was purified by flash chromatography on silica gel using a linear gradient of CyHex/EtOAc as eluents to give title compound (4.1 g, 61%). $^1$H NMR (300 MHz, $CD_2Cl_2$) δ ppm: 8.41-8.36 (m, 1H), 7.54-7.51 (m, 1H), 7.41-7.29 (m, 5H), 7.18-7.16 (m, 1H), 7.08-6.98 (m, 1H), 5.10 (s, 2H), 4.56-4.45 (m, 3H), 4.01-3.93 (m, 2H). [ES+MS] m/z 301 (MH$^+$).

Intermediate 6: Benzyl 3-(2-pyridylsulfonyl)azetidine-1-carboxylate

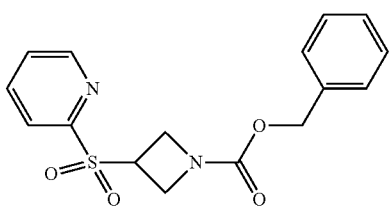 [SMILES: O=C(OCc1ccccc1)N1CC(S(=O)(=O)c2ccccn2)C1]

Ruthenium trichloride hydrate (SIGMA-ALDRICH, 13.9 mg, 0.07 mmol) was added followed by portion-wise addition of sodium metaperiodate (SIGMA-ALDRICH, 17.3 g, 80.7 mmol) in a solution of Intermediate 5 (4.04 g, 13.45 mmol) in EtOAc/$H_2O$ (30 mL/30 mL) at 0° C. The reaction was allowed to stir for 1 h at rt. Upon completion of the reaction, diethyl ether (50 mL) was added and the reaction was stirred for 30 min. Water was added (50 mL) and the layers were separated. The aq. phase was extracted with EtOAc (×2) and the organics were dried over (anh) $MgSO_4$ and concentrated under reduced pressure. The residue was purified by flash chromatography on silica gel using a linear gradient of CyHex/EtOAc as eluents to give title compound (4.4 g, 98%) as a colorless oil. $^1$H NMR (300 MHz, $CD_2Cl_2$) δ ppm: 8.72-8.69 (m, 1H), 8.11-8.08 (m, 1H), 8.04-8.01 (m, 1H), 7.63-7.58 (m, 1H), 7.43-7.30 (m, 5H), 5.10 (s, 2H), 4.49-4.40 (m, 3H), 4.27 (t, J=9.0 Hz, 2H). [ES+MS] m/z 333 (MH$^+$).

Intermediate 7: (1-benzyloxycarbonylazetidin-3-yl)sulfonyl Sodium

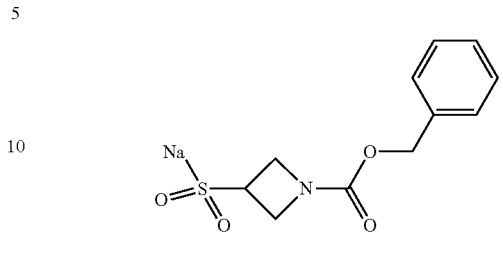

Ethanethiol (SIGMA-ALDRICH, 6.58 mL, 91.2 mmol) was added slowly into a suspension of NaH 60% (SIGMA-ALDRICH, 1.56 g, 39.1 mmol) in THF (20 mL) at 0° C. under argon atmosphere After stirring at 0° C. for 5 min, the reaction mixture was added dropwise in a THF (10 mL) solution of Intermediate 6 (4.33 g, 13.0 mmol) at 0° C. The mixture was stirred at 0° C. for 2 h, then at rt for 10 h. After the removal of solvent under vacuum, the residue was treated with $H_2O$ (20 mL) and the pH was adjusted to 7 with HCl (1 M) and sodium bicarbonate (saturated solution). The aq. layer was washed with diethylether to remove 2-(ethylthio)pyridine and ethanethiol. The aq. phase was concentrated and the residue was purified by preparative HPLC (OmniSphere C18 column, 10μ, 41×250 mm) gradient 15 min 5% to 50% ACN/$H_2O$ (0.1% formic acid) then 5 min 100% ACN to yield the title compound (2.9 g, 80%) as a colorless oil. [ES–MS] m/z 254 (M–Na).

Intermediate 8: benzyl 3-[4-(trifluoromethyl)-2-pyridyl]azetidine-1-carboxylate

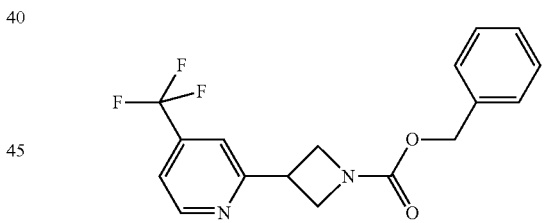

To a solution of 4-(trifluoromethyl)pyridine (SIGMA ALDRICH, 59 μL, 0.51 mmol), p-TsOH.$H_2O$ (ACROS, 97 mg, 0.51 mmol), Intermediate 7 (282.7 mg, 1.02 mmol) and Zinc chloride (ACROS, 104.2 mg, 0.76 mmol) in $H_2O$ (4 mL) and diethyl carbonate (6 mL), was added tert-butyl hydroperoxide (SIGMA ALDRICH, 0.28 ml, 2.04 mmol) by slow addition at 0° C. with vigorous stirring. After 5 min, the reaction was heated to 90° C. and stirred for 1 h. The resulting mixture was diluted with DCM and saturated aq. solution of $K_2CO_3$. The organic layer was dried over (anh) $Na_2SO_4$, concentrated under reduce pressure, and the residue was purified by flash column chromatography using a linear gradient of CyHex/EtOAc as eluents to afford title compound (46 mg, 27%). $^1$H NMR (300 MHz, $CD_2Cl_2$) δ ppm: 8.89-8.79 (m, 1H), 7.50-7.25 (m, 7H), 5.13 (s, 2H), 4.41 (t, J=8.5 Hz, 2H), 4.34-4.19 (m, 2H), 4.07-3.98 (m, 1H). [ES+MS] m/z 337 (MH$^+$).

Intermediate 9: benzyl 3-[5-(trifluoromethyl)-2-pyridyl]azetidine-1-carboxylate

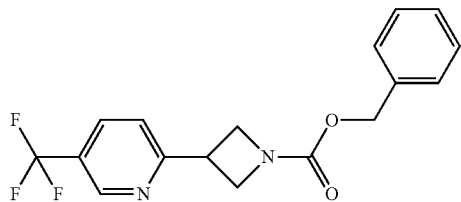 [SMILES: O=C(OCc1ccccc1)N1CC(c2ccc(C(F)(F)F)cn2)C1]

Intermediate 9 was prepared using an analogous method to that described for Intermediate 8 but replacing 4-(trifluoromethyl)pyridine with 3-(trifluoromethyl)pyridine (SIGMA-ALDRICH, 0.68 mmol). $^1$H NMR (300 MHz, CD$_2$Cl$_2$) δ ppm: 9.03-8.87 (m, 1H), 8.01-7.82 (m, 1H), 7.48-7.26 (m, 6H), 5.15 (s, 2H), 4.42 (t, J=8.6 Hz, 2H), 4.33-4.21 (m, 2H), 4.08-3.97 (m, 1H). [ES+MS] m/z 337 (MH$^+$).

Intermediate 10: 2-(azetidin-3-yl)-4-(trifluoromethyl)pyridine

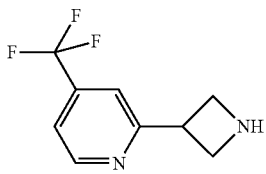 [SMILES: FC(F)(F)c1ccnc(C2CNC2)c1]

To a stirred solution of Intermediate 8 (53 mg, 0.16 mmol) and 10% Pd—C(ALFA-AESAR, 10-20% by weight) in MeOH (0.5 mL) was added neat triethylsilane (SIGMA-ALDRICH, 251.7 µL, 1.58 mmol) dropwise from a pressure-equalizing dropping funnel under an argon-filled balloon. When the reaction was complete (1 h, TLC), the mixture was filtered through celite and the solvent was removed in vacuo to give title compound which was used in the next step without further purification. [ES+MS] m/z 203 (MH$^+$).

Intermediate 11: 2-(azetidin-3-yl)-5-(trifluoromethyl)pyridine

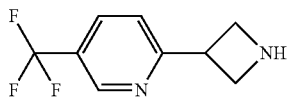 [SMILES: FC(F)(F)c1ccc(C2CNC2)nc1]

Intermediate 11 was prepared using an analogous method to that described for Intermediate 10 but replacing Intermediate 8 with Intermediate 9 (0.18 mmol). [ES+MS] m/z 203 (MH$^+$).

Intermediate 12: 1-(benzotriazol-1-yl)-4,4,4-trifluoro-butan-1-one

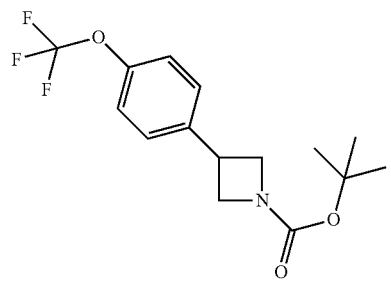 [SMILES: CC(C)(C)OC(=O)N1CC(c2ccc(OC(F)(F)F)cc2)C1]

[4-(Trifluoromethoxy)phenyl]boronic acid (FLUOROCHEM, 206 mg, 1.0 mmol), NiI$_2$ (ALFA-AESAR, 9.38 mg, 0.03 mmol), trans-2-aminocyclohexanol hydrochloride (SIGMA-ALDRICH, 4.55 mg, 0.03 mmol) and potassium hexamethyldisilazane (SIGMA-ALDRICH, 199.5 mg, 1.00 mmol) were weighed into a microwave vial. The mixture was then capped and placed under an argon atmosphere. Isopropanol (1.0 mL) was added and the mixture was stirred under nitrogen for 2 h. Tert-butyl 3-iodoazetidine-1-carboxylate (FLUOROCHEM, 141.6 mg, 0.50 mmol) in solution of Isopropanol (0.25 mL+0.25 mL rinse) was quickly added. The argon atmosphere was removed and the mixture was heated at 80° C. for 30 min. After allowing to rt, the mixture was diluted with EtOH (5 mL) and filtered through a plug of celite. The filter cake was rinsed two times with EtOH (2×5 mL) and the filtrate was concentrated under vacuum to give crude yellow oil. The residue was purified on flash chromatography using a linear gradient of CyHex/EtOAc as eluents to yield title compound (102 mg, 61%). $^1$H NMR (300 MHz, CDCl$_3$) δ ppm: 7.34 (d, J=8.6 Hz, 2H), 7.20 (d, J=8.6 Hz, 2H), 4.34 (t, J=8.5 Hz, 2H), 3.95 (m, 2H), 3.78-3.68 (m, 1H), 1.47 (s, 9H). [ES+MS] m/z 318 (MH$^+$).

Intermediates 13-33 were prepared by methods analogous to that described for Intermediate 12 but replacing the boronic acid with that indicated in Table 1. Modifications in the purification step are also indicated.

TABLE 1

| Int. | Structure | Boronic acid | Physical data |
|---|---|---|---|
| 13 | ![structure] See footnote a) | ![boronic acid] SIGMA-ALDRICH | $^1$H NMR (300 MHz, CD$_2$Cl$_2$) δ ppm: 7.36 (d, J = 8.5 Hz, 2H), 7.29 (d, J = 8.5 Hz, 2H), 4.32 (t, J = 8.6 Hz, 2H), 3.94-3.89 (m, 2H), 3.78-3.68 (m, 1H), 1.47 (s, 9H). [ES+ MS] m/z 268, 270 (MH$^+$). |

TABLE 1-continued

| Int. | Structure | Boronic acid | Physical data |
|---|---|---|---|
| 14 | 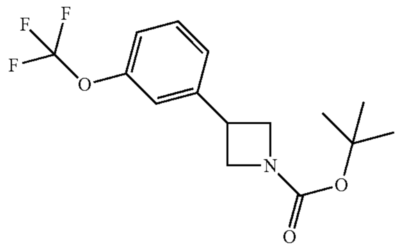 [SMILES: CC(C)(C)OC(=O)N1CC(c2cccc(OC(F)(F)F)c2)C1] | FLUOROCHEM | $^1$H NMR (300 MHz, CDCl$_3$) δ ppm: 7.38 (t, J = 7.7 Hz, 1H), 7.27 (d, J = 7.7 Hz, 1H), 7.15 (s, 1H), 7.17-7.09 (m, 1H), 4.35 (t, J = 8.5 Hz, 2H), 3.99-3.93 (m, 2H), 3.80-3.70 (m, 1H), 1.48 (s, 9H). [ES+ MS] m/z 318 (MH$^+$). |
| 15 | 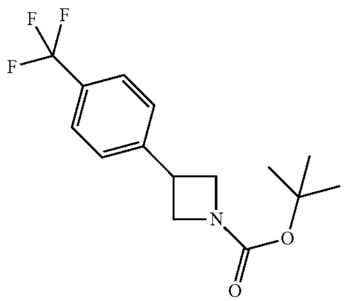 [SMILES: CC(C)(C)OC(=O)N1CC(c2ccc(C(F)(F)F)cc2)C1] | SIGMA-ALDRICH | $^1$H NMR (300 MHz, CDCl$_3$) δ ppm: 7.62 (d, J = 8.2 Hz, 2H), 7.44 (d, J = 8.2 Hz, 2H), 4.37 (t, J = 8.8 Hz, 2H), 3.99-3.94 (m, 2H), 3.84-3.74 (m, 1H), 1.48 (s, 9H). [ES+ MS] m/z 302 (MH$^+$). |
| 16 | 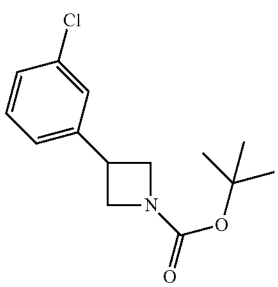 | AVOCADO | $^1$H NMR (300 MHz, CDCl$_3$) δ ppm: 7.34-7.27 (m, 2H), 7.26-7.24 (m, 1H), 7.23-7.17 (m, 1H), 4.34 (t, J = 8.9 Hz, 2H), 3.99-3.94 (m, 2H), 3.75-3.69 (m, 1H), 1.49 (s, 9H). [ES+ MS] m/z 268, 270 (MH$^+$). |
| 17 | 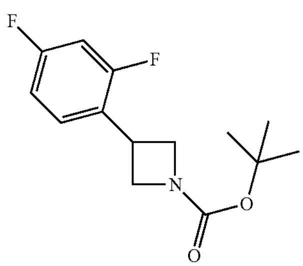 [SMILES: CC(C)(C)OC(=O)N1CC(c2ccc(F)cc2F)C1] | SIGMA-ALDRICH | $^1$H NMR (300 MHz, CDCl$_3$) δ ppm: 7.37-27 (m, 1H), 6.94-6.75 (m, 2H), 4.33 (t, J = 8.3 Hz, 2H), 4.05-3.91 (m, 3H), 1.47 (s, 9H). [ES+ MS] m/z 270 (MH$^+$). |
| 18 | 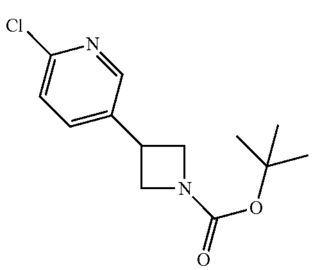 | ACROS | $^1$H NMR (300 MHz, CDCl$_3$) δ ppm: 8.29 (d, J = 2.5 Hz, 1H), 7.72-7.65 (m, 1H), 7.34 (d, J = 8.3 Hz, 1H), 4.37 (t, J = 8.8 Hz, 2H), 3.93-3.86 (m, 2H), 3.77-3.66 (m, 1H), 1.46 (s, 9H). [ES+ MS] m/z 269, 271 (MH$^+$). |

See footnote b)

TABLE 1-continued

| Int. | Structure | Boronic acid | Physical data |
|---|---|---|---|
| 19 | (4-fluoro-2-chlorophenyl azetidine Boc) | 4-fluoro-2-chlorophenylboronic acid / ALFA-AESAR | ¹H NMR (300 MHz, CD₂Cl₂) δ ppm: 7.45-7.40 (m, 1H), 7.19-7.15 (m, 1H), 7.11-7.04 (m, 1H), 4.34 (t, J = 8.1 Hz, 2H), 4.14-4.04 (m, 1H), 4.00-3.95 (m, 2H), 1.46 (s, 9H). [ES+ MS] m/z 286, 288 (MH⁺). |
| 20 | (6-trifluoromethylpyridin-3-yl azetidine Boc) See footnote b) | 6-(trifluoromethyl)pyridine-3-boronic acid / FLUOROCHEM | ¹H NMR (300 MHz, CDCl₃) δ ppm: 8.67 (d, J = 2.0 Hz, 1H), 7.95-7.92 (m, 1H), 7.73 (d, J = 8.1 Hz, 1H), 4.40 (t, J = 8.9 Hz, 2H), 3.99-3.94 (m, 2H), 3.87-3.83 (m, 1H), 1.47 (s, 9H). [ES+ MS] m/z 303 (MH⁺). |
| 21 | (6-methoxypyridin-3-yl azetidine Boc) See footnote b) | 6-methoxypyridine-3-boronic acid / FLUOROCHEM | ¹H NMR (300 MHz, CDCl₃) δ ppm: 8.05 (d, J = 2.5 Hz, 1H), 7.67-7.64 (m, 1H), 6.78 (d, J = 8.5 Hz, 1H), 4.31 (t, J = 8.8 Hz, 2H), 3.92 (s, 3H), 3.92-3.86 (m, 2H), 3.73-3.67 (m, 1H), 1.46 (s, 9H). [ES+ MS] m/z 265 (MH⁺). |
| 22 | (5-chloropyridin-3-yl azetidine Boc) See footnote b) | 5-chloropyridine-3-boronic acid / FLUOROCHEM | ¹H NMR (300 MHz, CDCl₃) δ ppm: 8.49 (d, J = 2.3 Hz, 1H), 8.43 (d, J = 2.3 Hz, 1H), 7.77-3.75 (m, 1H), 4.37 (t, J = 8.9 Hz, 2H), 3.95-3.90 (m, 2H), 3.78-3.74 (m, 1H), 1.47 (s, 9H). [ES+ MS] m/z 269, 271 (MH⁺). |
| 23 | (5-trifluoromethylpyridin-3-yl azetidine Boc) See footnote b) | 5-(trifluoromethyl)pyridine-3-boronic acid / ACROS | ¹H NMR (300 MHz, CDCl₃) δ ppm: 8.81 (d, J = 2.0 Hz, 1H), 8.76 (d, J = 2.0 Hz, 1H), 7.98-7.95 (m, 1H), 4.40 (t, J = 8.7 Hz, 2H), 3.99-3.94 (m, 2H), 3.87-3.83 (m, 1H), 1.47 (s, 9H). [ES+ MS] m/z 303 (MH⁺). |

TABLE 1-continued

| Int. | Structure | Boronic acid | Physical data |
|---|---|---|---|
| 24 | (4-fluoro-2-(trifluoromethyl)phenyl azetidine N-Boc) | 4-fluoro-2-(trifluoromethyl)phenylboronic acid; FLUOROCHEM | ¹H NMR (300 MHz, CDCl₃) δ ppm: 7.76-7.69 (m, 1H), 7.36-7.27 (m, 2H), 4.33 (t, J = 8.6 Hz, 2H), 4.16-4.04 (m, 1H), 3.97-3.88 (m, 2H), 1.47 (s, 9H). [ES+ MS] m/z 320 (MH⁺). |
| 25 | (pyridin-3-yl azetidine N-Boc) | pyridin-3-ylboronic acid; LANCASTER | ¹H NMR (300 MHz, CDCl₃) δ ppm: 8.54 (d, J = 2.2 Hz, 1H), 8.54-8.49 (m, 1H), 7.75-7.71 (m, 1H), 7.35-7.30 (m, 1H), 4.35 (t, J = 8.8 Hz, 2H), 3.97-3.93 (m, 2H), 3.82-3.72 (m, 1H), 1.47 (s, 9H). [ES+ MS] m/z 235 (MH⁺). |
| 26 | (3,4-difluorophenyl azetidine N-Boc) | 3,4-difluorophenylboronic acid; SIGMA-ALDRICH | ¹H NMR (300 MHz, CDCl₃) δ ppm: 7.19-7.09 (m, 2H), 7.05-6.99 (m, 1H), 4.33 (t, J = 8.6 Hz, 2H), 3.93-3.88 (m, 2H), 1.47 (s, 9H). [ES+ MS] m/z 270 (MH⁺). |
| 27 | (4-fluoro-2-methylphenyl azetidine N-Boc) | 4-fluoro-2-methylphenylboronic acid; FLUOROCHEM | ¹H NMR (300 MHz, CDCl₃) δ ppm: 7.32-7.29 (m, 1H), 6.95-6.89 (m, 1H), 6.89-6.85 (m, 1H), 4.31 (t, J = 8.4 Hz, 2H), 4.01-3.95 (m, 2H), 3.99-3.84 (m, 1H), 2.21 (s, 3H), 1.46 (s, 9H). [ES+ MS] m/z 266 (MH⁺). |
| 28 | (3-fluorophenyl azetidine N-Boc) | 3-fluorophenylboronic acid; LANCASTER | ¹H NMR (300 MHz, CDCl₃) δ ppm: 7.34-7.28 (m, 1H), 7.09 (d, J = 7.9 Hz, 1H), 7.10-7.00 (m, 1H), 6.99-6.93 (m, 1H), 4.34 (t, J = 8.8 Hz, 2H), 3.99-3.94 (m, 2H), 3.76-3.70 (m, 1H), 1.48 (s, 9H). [ES+ MS] m/z 252 (MH⁺). |
| 29 | (pyridin-4-yl azetidine N-Boc) | pyridin-4-ylboronic acid; MATRIX | ¹H NMR (300 MHz, CDCl₃) δ ppm: 7.30 (d, J = 4.2 Hz, 2H), 7.26 (d, J = 4.2 Hz, 1H), 4.36 (t, J = 8.6 Hz, 2H), 4.00-3.95 (m, 2H), 3.74-3.69 (m, 1H), 1.48 (s, 9H). [ES+ MS] m/z 235 (MH⁺). |

TABLE 1-continued

| Int. | Structure | Boronic acid | Physical data |
|---|---|---|---|
| 30 | 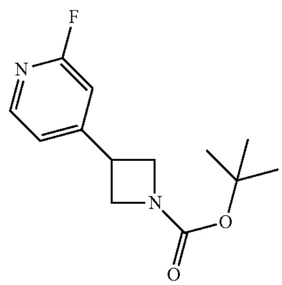 [SMILES: CC(C)(C)OC(=O)N1CC(c2ccnc(F)c2)C1] | APOLLO | ¹H NMR (300 MHz, CDCl₃) δ ppm: 8.19 (d, J = 5.2 Hz, 1H), 7.15-7.13 (m, 1H), 6.87 (br s, 1H), 4.35 (t, J = 8.7 Hz, 2H), 3.97-3.92 (m, 2H), 3.78-3.70 (m, 1H), 1.46 (s, 9H). [ES+ MS] m/z 253 (MH⁺). |
| 31 | 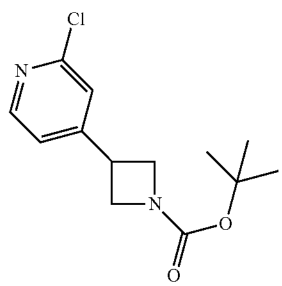 [SMILES: CC(C)(C)OC(=O)N1CC(c2ccnc(Cl)c2)C1] | APOLLO | ¹H NMR (300 MHz, CDCl₃) δ ppm: 8.35 (d, J = 5.3 Hz, 1H), 7.28 (s, 1H), 7.17 (d, J = 5.3 Hz, 1H), 4.34 (t, J = 8.8 Hz, 2H), 3.96-3.91 (m, 2H), 3.72-3.64 (m, 1H), 1.46 (s, 9H). [ES+ MS] m/z 269, 270 (MH⁺). |
| 32 | 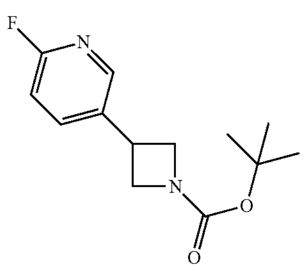 [SMILES: CC(C)(C)OC(=O)N1CC(c2ccc(F)nc2)C1] | FLUOROCHEM | ¹H NMR (300 MHz, CDCl₃) δ ppm: 8.10 (s, 1H), 7.86-7.80 (m, 1H), 6.97-3.93 (m, 1H), 4.36 (t, J = 8.8 Hz, 2H), 3.95-3.88 (m, 2H), 3.78-3.69 (m, 1H), 1.46 (s, 9H). [ES+ MS] m/z 253 (MH⁺). |
| 33 | | SIGMA-ALDRICH | ¹H NMR (300 MHz, CDCl₃) δ ppm: 6.96-3.91 (m, 2H), 4.32 (t, J = 8.9 Hz, 2H), 3.89-3.85 (m, 2H), 3.69-3.58 (m, 1H), 1.46 (s, 9H). [ES+ MS] m/z 288 (MH⁺). | a) Purified by preparative HPLC (Varian, ACN/H₂O/HCOOH 0.1% 10/90 to 100/0)

b) Purification with gradient DCM pure to DCM/MeOH 98/2

Intermediate 34: tert-butyl 3-(4-cyanophenyl)azetidine-1-carboxylate

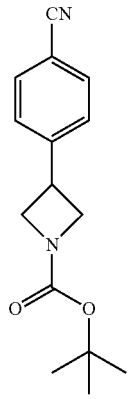 [SMILES: CC(C)(C)OC(=O)N1CC(c2ccc(C#N)cc2)C1]

To a stirred solution of tert-butyl 3-iodoazetidine-1-carboxylate (CNH TECHNOLOGIES, 2 g, 7.067 mmol), (4-cyanophenyl)boronic acid (COMBIBLOCKS, 2 g, 14.134 mmol) in isopropyl alcohol (20 mL) were added NiI$_2$ (SIGMA-ALDRICH, 132 mg, 0.424 mmol) and trans-2-amino cyclohexanol hydrochloride (SIGMA-ALDRICH, 64 mg, 0.424 mmol) at 26° C. The reaction mixture was degassed with argon for 10 min, followed by the addition of sodium hexamethyldisilazane (1M in THF) (HYCHEM, 14 mL, 14.134 mmol) at 26° C. The reaction mixture was heated to 80° C. for 1.5 h in microwave. The reaction mixture was quenched with saturated ammonium chloride solution (100 mL) and extracted with EtOAc (3×200 mL). The organic layer was washed with brine solution (100 mL), dried over (anh) Na$_2$SO$_4$, filtered and concentrated under reduced pressure. The crude compound was purified by silica chromatography column using a linear gradient of petroleum ether/EtOAc as eluents to yield the title compound (1.1 g, 58%) as a pale yellow liquid. $^1$H NMR (400 MHz, CDCl$_3$) δ ppm: 7.65 (d, J=8.3 Hz, 2H) 7.43 (d, J=8.1 Hz, 2H) 4.40-4.33 (m, 2H) 3.97-3.91 (m, 2H) 3.82-3.73 (m, 1H) 1.47 (s, 9H). [ES+MS] m/z 203 (M-57).

Intermediate 35: tert-butyl 3-(3,6-dihydro-2H-pyran-4-yl)azetidine-1-carboxylate

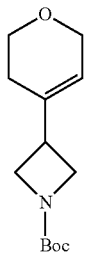 [SMILES: CC(C)(C)OC(=O)N1CC(C2=CCOCC2)C1]

To a stirred solution of tert-butyl 3-iodoazetidine-1-carboxylate (CNH TECHNOLOGIES, 2 g, 7.067 mmol), and 2-(3,6-dihydro-2H-pyran-4-yl)-4,4,5,5-tetramethyl-1,3,2-dioxaborolane (OAKWOOD, 2.37 g, 11.307 mmol) in isopropyl alcohol (20 mL) were added sequentially NiI$_2$ (STREM, 221 mg, 0.7067 mmol) and (1R, 2R) trans-2-amino cyclohexanol hydrochloride (COMBIBLOCKS, 107 mg, 0.7067 mmol) at 26° C. The reaction mixture was degassed with nitrogen for 15 min and stirred for 10 min at 26° C., followed by the addition of sodium hexamethyldisilazane (1M in THF) (HYCHEM, 14 mL, 14.134 mmol) at 26° C. The reaction mixture was heated to 80° C. and stirred for 16 h at the same temperature. The reaction mixture was quenched with saturated ammonium chloride solution (100 mL) and extracted with EtOAc (3×100 mL). The organic layer was dried over (anh) Na$_2$SO$_4$, filtered and concentrated under reduced pressure. The crude was purified by silica chromatography column using a linear gradient of petroleum ether/EtOAc to yield the title compound (750 mg, 44%) as a brown liquid. $^1$H NMR (400 MHz, CDCl$_3$) δ ppm 5.54 (br d, J=1.3 Hz, 1H), 4.21-4.10 (m, 2H), 4.01 (t, J=8.7 Hz, 2H), 3.90-3.75 (m, 4H), 3.20-3.08 (m, 1H), 2.09 (br t, J=2.4 Hz, 2H), 1.43 (s, 9H). [ES+MS] m/z 240 (MH$^+$).

Intermediate 36: tert-butyl 3-(4,4-difluorocyclohex-1-en-1-yl)azetidine-1-carboxylate

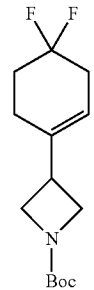 [SMILES: CC(C)(C)OC(=O)N1CC(C2=CCC(F)(F)CC2)C1]

Intermediate 36 was prepared by method analogous to that described for Intermediate 35 but replacing 2-(3,6-dihydro-2H-pyran-4-yl)-4,4,5,5-tetramethyl-1,3,2-dioxaborolane with 2-(4,4-difluorocyclohex-1-en-1-yl)-4,4,5,5-tetramethyl-1,3,2-dioxaborolane (COMBIBLOCKS). $^1$H NMR (400 MHz, CDCl$_3$) δ ppm: 5.40 (br d, J=1.3 Hz, 1H), 4.03 (t, J=8.6 Hz, 2H), 3.84-3.78 (m, 2H), 3.23-3.12 (m, 1H), 2.63-2.46 (m, 2H), 2.30-2.21 (m, 2H), 2.12-1.98 (m, 2H), 1.44 (s, 9H).

Intermediate 37: tert-butyl 3-(tetrahydro-2H-pyran-4-yl)azetidine-1-carboxylate

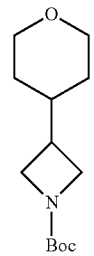 [SMILES: CC(C)(C)OC(=O)N1CC(C2CCOCC2)C1]

To a solution of Intermediate 35 (750 mg, 3.138 mmol) in MeOH (20 mL) was added 10% Pd/C (HINDUSTAN, 500 mg) at 27° C. The reaction mixture was stirred for 4 h under hydrogen atmosphere (balloon pressure) at the same temperature. The reaction mixture was filtered through celite pad and concentrated under reduced pressure to yield the title compound (700 mg, 92%) as a brown gum. $^1$H NMR (400 MHz, CDCl₃) δ ppm: 4.05-3.85 (m, 4H), 3.70-3.60 (m, 2H), 3.40-3.32 (m, 2H), 2.36-2.15 (m, 1H), 1.74-1.64 (m, 1H), 1.58-1.50 (m, 2H), 1.44 (s, 9H), 1.26-1.18 (m, 2H).

Intermediate 38: tert-butyl 3-(4,4-difluorocyclohexyl)azetidine-1-carboxylate

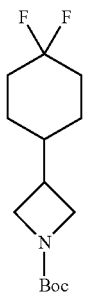 [SMILES: CC(C)(C)OC(=O)N1CC(C2CCC(F)(F)CC2)C1]

Intermediate 38 was prepared by method analogous to that described for Intermediate 37 but replacing Intermediate 35 with Intermediate 36. ¹H NMR (400 MHz, CDCl₃) δ ppm: 3.97 (t, J=8.6 Hz, 2H), 3.67-3.59 (m, 2H), 2.33-2.21 (m, 1H), 2.16-2.03 (m, 2H), 1.82-1.58 (m, 4H), 1.53-1.47 (m, 1H), 1.44 (s, 9H), 1.31-1.13 (m, 2H). [ES+MS] m/z 275 (M).

Intermediate 39: tert-butyl 3-(3,5-difluoro-2-pyridyl)azetidine-1-carboxylate

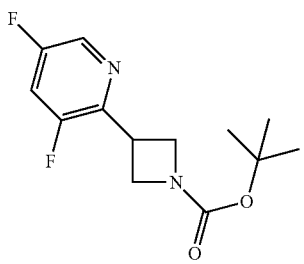 [SMILES: CC(C)(C)OC(=O)N1CC(c2ncc(F)cc2F)C1]

Lithium chloride (SIGMA-ALDRICH, 316.3 mg, 7.46 mmol) was added to a Schlenk tube equipped with a magnetic stir bar and a rubber septum and was heated with a heat gun for 10 min under vacuum and backfilled with argon 3 times. Zinc powder (SIGMA-ALDRICH, 487.9 mg, 7.46 mmol) was weighed and added to the tube after cooling to room temperature. The powders were again heated with a heat gun for 10 min under vacuum and backfilled with argon 3 times. After cooling to rt, THF (5 mL) and Iodine (ALFA AESAR, 23.7 mg, 0.09 mmol) were added and heated at 60° C. in an oil bath for 20 min. After cooling at rt, tert-butyl 3-iodoazetidine-1-carboxylate (ACTIVATE SCIENTIFIC, 647 μL, 3.73 mmol) was added and the grey reaction mixture was replaced in the oil bath at 50° C. during 22 h. After cooling at rt, Pd(PPh₃)₂Cl₂ (ACROS, 47.1 mg, 0.07 mmol) and 2-bromo-3,5-difluoro-pyridine (ENAMINE, 133 μL, 1.24 mmol) were added to the Schlenk tube at 0° C. The mixture was stirred 4.5 h.

The black reaction mixture was then quenched by addition of saturated aq. NH₄Cl solution and extracted with EtOAc (×3). The organic layer was washed with brine, dried over (anh) MgSO₄ and concentrated in vacuo. The resulting residue was purified by flash chromatography using a linear gradient of DCM/MeOH as eluents to afford title compound (0.4 g, 79%) as a yellow oil. ¹H NMR (300 MHz, CD₂Cl₂) δ ppm: 8.40 (d, J=2.4 Hz, 1H), 7.29-7.19 (m, 1H), 4.30-4.08 (m, 5H), 1.46 (s, 9H). [ES+MS] m/z 279 (MH⁺).

Intermediate 40: tert-butyl 3-(4-chloro-2-pyridyl)azetidine-1-carboxylate

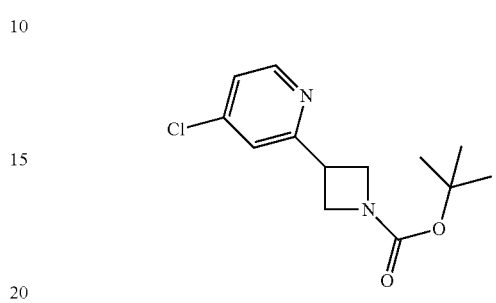

Intermediate 40 was prepared by method analogous to that described for Intermediate 39 but replacing the 2-bromo-3,5-difluoro-pyridine with 2-bromo-4-chloro-pyridine (FLUOROCHEM, 1.25 mmol). ¹H NMR (300 MHz, CD₂Cl₂) δ ppm: 8.53 (d, J=5.3 Hz, 1H), 7.27 (d, J=2.0 Hz, 1H), 7.27-7.22 (m, 1H), 4.29-4.24 (m, 2H), 4.13-4.08 (m, 2H), 3.89-3.81 (m, 1H), 1.46 (s, 9H). [ES+MS] m/z 269, 271 (MH⁺).

Intermediate 41: tert-butyl 3-[2-(trifluoromethyl)-4-pyridyl]azetidine-1-carboxylate

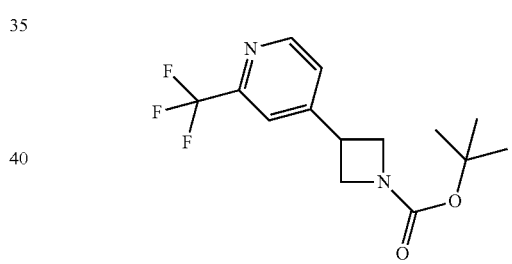

A 20 mL screw-cap vial equipped with a magnetic stir bar and fitted with a teflon blow out septum was charged with Zinc powder (SIGMA ALDRICH, 163 mg, 2.50 mmol), XPhos-Pd-precatalyst (*Angew. Chem. Int. Ed.* 2016, 55, 1849-1853, 43 mg, 5 mmol %), sodium octanoate (FLUOROCHEM, 83 mg, 0.5 mmol), sodium chloride (VWR, 116 mg, 2.00 mmol).

The reaction tube was evacuated and backfilled with argon (3 times). 4-bromo-2-(trifluoromethyl)pyridine (APOLLO, 123.7 μL, 1.00 mmol), tert-butyl 3-iodoazetidine-1-carboxylate (ACTIVATE SCIENTIFIC, 260 μL, 1.50 mmol), TMEDA (SIGMA-ALDRICH, 377 μL, 2.50 mmol), 1-octanol (LANCASTER, 237 μL, 1.50 mmol) and degassed water (3.3 mL) were then added. The screw-cap septum was quickly replaced by a new unpunctured septum under a flow of argon and the reaction mixture was stirred at 45° C. for 36 h. The tube was cooled to rt and diluted with EtOAc. After shaking the reaction mixture, the contents were filtered through a small pad of Celite. The reaction tube and the Celite bed were washed with an additional 50 mL of EtOAc. The combined filtrates were transferred to a separating funnel and washed with 0.3M aq. solution of HCl (×2) and 0.3N aq. solution of NaOH (×2). The organic layer was separated, dried over (anh) Na₂SO₄, filtered and concentrated under reduced pressure. The crude product was purified by flash chromatography using a linear gradient of DCM/MeOH to give title compound (100 mg, 15%) as yellow oil. ¹H NMR (300 MHz, CD₂Cl₂) δ ppm: 8.69 (d, J=5 Hz, 1H), 7.69-7.65 (m, 1H), 7.51-7.47 (m, 1H), 4.38 (t, J=8.7 Hz, 2H), 3.99-3.93 (m, 2H), 3.89-3.76 (m, 1H), 1.46 (s, 9H). [ES+MS] m/z 303 (MH⁺).

Intermediate 42: tert-butyl 3-(5-fluoro-2-pyridyl)azetidine-1-carboxylate

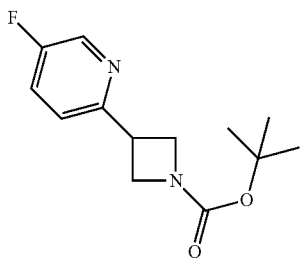 [SMILES: CC(C)(C)OC(=O)N1CC(c2ccc(F)cn2)C1]

Zinc dust (SIGMA-ALDRICH) was slowly added to a well stirred solution of aq. 2N HCl (FISHER SCIENTIFIC, 6 mL). The material was allowed to stir for 30 min at which point it was filtered, washed with water, EtOH, and diethyl ether. The material was dried under reduced pressure.

A round bottom flask fitted with a magnetic stirrer under argon was charged with Zinc Dust (SIGMA-ALDRICH, 138 mg, preactivated according to the above preparation, 2.1 mmol) and DMA (0.5 mL, anh). 1,2-dibromoethane (ALFA-AESAR, 14 μL, 0.158 mmol) was then added slowly, followed by slowly addition of TMSCI (SIGMA-ALDRICH, 20 μL, 0.158 mmol, 0.15 eq). The reaction mixture was stirred for 30 min at rt. A solution of tert-butyl 3-iodo-azetidine-1-carboxylate (ACTIVATE SCIENTIFIC, 0.275 mL, 1.583 mmol) in DMA (1 mL, anh) was added over 5 min at 65° C. using a water bath. The suspension was stirred for 1 h at rt at which point it was degassed with argon. Stirring was stopped and the suspension was allowed to stand. A sealed tube was charged with 2-bromo-5-fluoropyridine (ENAMINE, 186 mg, 1.06 mmol), PdCl₂dppf.CH₂Cl₂ (SIGMA-ALDRICH, 25.8 mg, 0.032 mmol, 0.03), CuI (SIGMA-ALDRICH, 12.5 mg, 0.065 mmol), and DMA (1 mL, anh). The solution was degassed with argon. The clear zinc reagent solution above the residual solid zinc was poured into the flask under argon. The brown solution was degassed with argon, the tube was sealed and heated to 80° C. for 17 h. Brine (5 mL) was added into the reaction mixture which was extracted with EtOAc. Aq. layer was washed twice with EtOAc. The organic layer was washed with brine, dried over (anh) MgSO₄ and concentrated. The residue was purified by flash chromatography using a linear gradient of DCM/MeOH to give title compound (103 mg, 26%) as an orange oil. ¹H NMR (300 MHz, CD₂Cl₂) δ ppm: 8.47 (d, J=2.9 Hz, 1H), 7.43-7.36 (m, 1H), 7.25-7.21 (m, 1H), 4.29-4.23 (m, 2H), 4.12-4.07 (m, 2H), 3.92-3.84 (m, 1H), 1.46 (s, 9H). [ES+MS] m/z 253 (MH⁺).

Intermediate 43: tert-butyl 3-(4,4-difluoro-1-piperidyl)azetidine-1-carboxylate

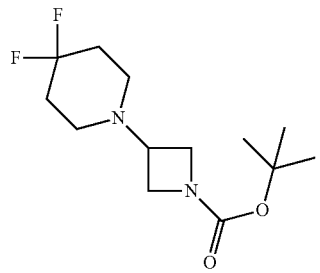 [SMILES: CC(C)(C)OC(=O)N1CC(N2CCC(F)(F)CC2)C1]

A mixture of 4,4-difluoropiperidine hydrochloride (FLUOROCHEM, 167 mg, 1.1 mmol), K₂CO₃ (SIGMA-ALDRICH, 390 mg, 2.8 mmol) and tert-butyl 3-iodoazetidine-1-carboxylate (FLUOROCHEM, 123 μL, 0.71 mmol) in ACN (3 mL) was heated in a microwave 50 apparatus (Anton Paar) to 120° C. for 1.5 h and then heated to 130° C. for 1 h. The resulting solution was concentrated to give a residue which was diluted with H₂O, and extracted with EtOAc. The organic extract was dried over (anh) MgSO₄ and concentrated to afford title compound (200 mg, quant.) as a yellow oil which was used in next step without further purification. [ES+MS] m/z 277 (MH⁺).

Intermediate 44: tert-butyl 3-(piperidin-1-yl)azetidine-1-carboxylate

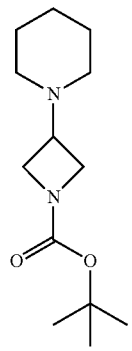 [SMILES: CC(C)(C)OC(=O)N1CC(N2CCCCC2)C1]

To a stirred solution of tert-butyl 3-oxoazetidine-1-carboxylate (ARK PHARMA, 1 g, 5.841 mmol) in DCM (10 mL) were added piperidine (AVRA, 744 mg, 8.762 mmol) and formic acid (SIGMA-ALDRICH, catalytic amount) at 0° C. The reaction mixture was allowed to 26° C. and stirred for 4 h at the same temperature. The reaction mixture was diluted with MeOH (10 mL) and followed by the portion-wise addition of sodium triacetoxy borohydride (ALFA AESAR, 2.47 g, 11.682 mmol) at 0° C. The resultant reaction mixture was allowed to 26° C. and stirred for 16 h at the same temperature. The reaction mixture was diluted with water (100 mL) and extracted with DCM (3×100 mL). Combined organic layers were washed with brine (100 mL), dried over (anh) Na₂SO₄, filtered and the concentrated under reduced pressure. The crude was purified by silica chromatography column using a linear gradient of petroleum ether/EtOAc as eluents to afford the title compound (800 mg, 52%) as a pale yellow liquid. [ES+MS] m/z 241 (MH⁺).

Intermediate 45: tert-butyl 3-(4-fluorophenyl)-3-hydroxyazetidine-1-carboxylate

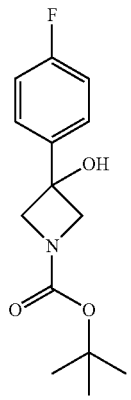 [SMILES: CC(C)(C)OC(=O)N1CC(O)(c2ccc(F)cc2)C1]

Method A:

To a solution of tert-butyl 3-oxoazetidine-1-carboxylate (ARKPHARMA, 5 g, 29.207 mmol,) in THF (50 mL) was added (4-fluorophenyl)magnesium bromide (2M in THF) (SIGMA-ALDRICH, 29.2 mL, 58.414 mmol,) dropwise at 0° C. The reaction mixture was allowed to 27° C. and stirred for 2 h. The reaction mixture was quenched with saturated ammonium chloride solution (50 mL) and extracted with EtOAc (2×100 mL). Combined organic layers were dried over (anh) Na$_2$SO$_4$, filtered and concentrated under reduced pressure. The crude was purified by silica chromatography column using a linear gradient of petroleum ether/EtOAc as eluents to afford the title compound (6.0 g, 80%) as a pale yellow solid. $^1$H NMR (400 MHz, CDCl$_3$) δ ppm: 7.51-7.45 (m, 2H), 7.12-7.05 (m, 2H), 4.27-4.21 (m, 2H), 4.19-4.13 (m, 2H), 2.49 (s, 1H), 1.47 (s, 9H). [ES+MS] m/z 268 (MH⁺).

Method B:

To the solution of tert-butyl 3-oxoazetidine-1-carboxylate (OAKWOOD, 1 g, 5.841 mmol), 1-bromo-4-fluorobenzene (ALFA AESAR, 1 g, 5.841 mmol) in THF (10 mL) was added n-butyl lithium (2.5M in hexane) (HYCHEM, 2.3 mL, 5.841 mmol) at −78° C. and was stirred for 2 h at that temperature. The reaction mixture was quenched with saturated ammonium chloride solution (100 mL) and extracted with EtOAc (3×150 mL). The organic layer was washed with brine (100 mL), dried over (anh) Na$_2$SO$_4$, filtered and concentrated under reduced pressure. The crude was purified by silica chromatography column using a linear gradient of petroleum ether/EtOAc as eluents to yield the title compound (700 mg, 33.65%) as a pale yellow liquid. $^1$H NMR (400 MHz, CDCl$_3$) δ ppm: 7.52-7.45 (m, 2H), 7.12-7.03 (m, 2H), 4.27-4.13 (m, 4H), 2.87 (br s, 1H), 1.46 (s, 9H). [ES+MS] m/z 212 (M−57).

Intermediate 46: tert-butyl 3-(4-fluorophenyl)-3-methoxyazetidine-1-carboxylate

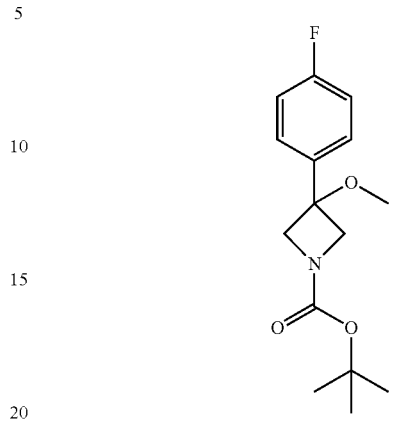

To a solution of Intermediate 45 (1 g, 3.741 mmol) in DMF (20 mL) was added 60% sodium hydride (ALFA AESAR, 300 mg, 7.482 mmol) in portionwise at 0° C. and stirred for 20 min at the same temperature, followed by the dropwise addition of methyl iodide (SYMAX FINECHEMICALS, 0.28 mL, 4.489 mmol) at 0° C. The reaction mixture was allowed to 27° C. and stirred for 2 h at the same temperature. The reaction mixture was quenched with ice cold water (50 mL) and extracted with EtOAc (2×50 mL). Combined organic layers were dried over (anh) Na$_2$SO$_4$, filtered and concentrated under reduced pressure. The crude was purified by silica chromatography column using a linear gradient of petroleum ether/EtOAc as eluents to afford the title compound (1.0 g, 95%) as a pale yellow liquid. $^1$H NMR (400 MHz, CDCl$_3$) δ ppm: 7.41-7.33 (m, 2H), 7.13-7.05 (m, 2H), 4.21-4.09 (m, 4H), 3.07 (s, 3H) 1.45 (s, 9H). [ES+MS] m/z 282 (M−100).

Intermediate 47: 2-(azetidin-3-yl)-5-fluoro-pyridine bis(2,2,2-trifluoroacetate)

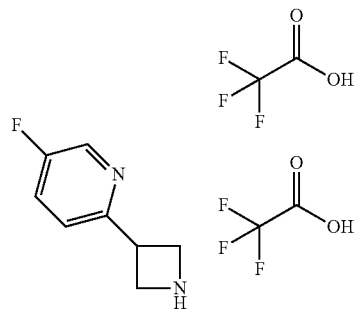

Intermediate 42 (103.0 mg, 0.41 mmol) was dissolved in 2 mL DCM. TFA (SIGMA-ALDRICH, 0.25 mL, 3.27 mmol) was added and the reaction mixture was stirred at rt for 1 h. The solvent was removed under reduced pressure by adding MeOH (ten times) in order to remove TFA excess, to give title compound (155.2 mg, 100%). [ES+MS] m/z 318 (MH⁺).

Intermediates 48-72 were prepared by method analogous to that described for Intermediate 47 but replacing the Intermediate 42 with that indicated in Table 2.

TABLE 2

| Int. | Structure | Starting Int. | Physical data |
| --- | --- | --- | --- |
| 48 | (4,4-difluoropiperidin-1-yl)-azetidine, bis-TFA salt<br>See footnote a) | 43 | [ES+ MS] m/z 177 (MH$^+$). |
| 49 | 3-(4-trifluoromethoxyphenyl)azetidine, TFA salt | 12 | [ES+ MS] m/z 218 (MH$^+$). |
| 50 | 3-(3-trifluoromethoxyphenyl)azetidine, TFA salt | 14 | [ES+ MS] m/z 218 (MH$^+$). |
| 51 | 3-(4-trifluoromethylphenyl)azetidine<br>See footnote b) | 15 | [ES+ MS] m/z 202 (MH$^+$). |
| 52 | 3-(3-chlorophenyl)azetidine<br>See footnote b) | 16 | [ES+ MS] m/z 168, 170 (MH$^+$). |
| 53 | 3-(2,4-difluorophenyl)azetidine, TFA salt | 17 | [ES+ MS] m/z 170 (MH$^+$). |

TABLE 2-continued
| Int. | Structure | Starting Int. | Physical data |
|---|---|---|---|
| 54 | 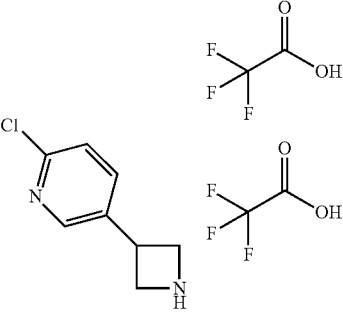<br>See footnote a) | 18 | [ES+ MS] m/z 169, 171 (MH+). |
| 55 | 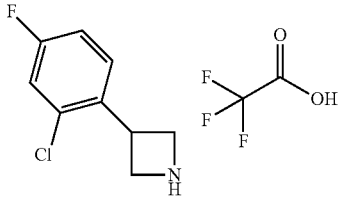 | 19 | [ES+ MS] m/z 186, 188 (MH+). |
| 56 | 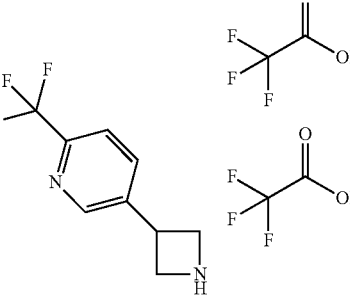<br>See footnote a) | 20 | [ES+ MS] m/z 203 (MH+). |
| 57 | 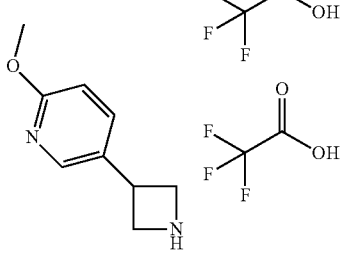<br>See footnote a) | 21 | [ES+ MS] m/z 165 (MH+). |

TABLE 2-continued
| Int. | Structure | Starting Int. | Physical data |
| --- | --- | --- | --- |
| 58 | 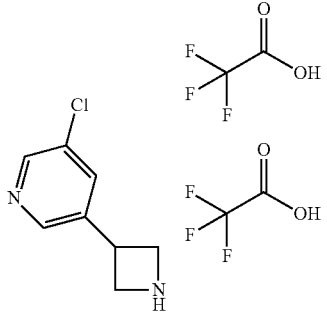 | 22 | [ES+ MS] m/z 169, 171 (MH+). |
| 59 | 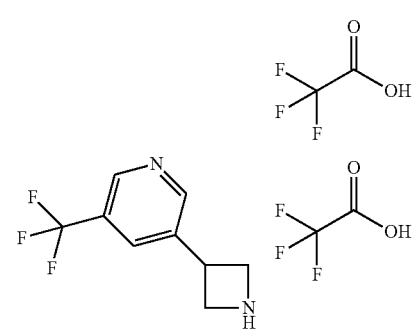 | 23 | [ES+ MS] m/z 203 (MH+). |
| 60 | 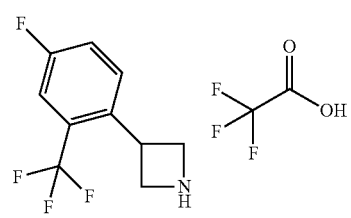 | 24 | [ES+ MS] m/z 220 (MH+). |
| 61 | 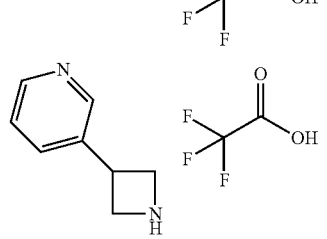 | 25 | [ES+ MS] m/z 135 (MH+). |
| 62 | 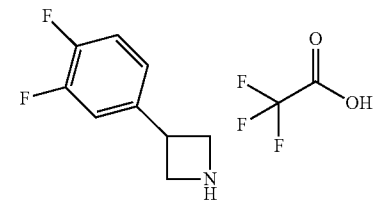 | 26 | [ES+ MS] m/z 170 (MH+). |
See footnote a)

TABLE 2-continued

| Int. | Structure | Starting Int. | Physical data |
|---|---|---|---|
| 63 | (4-fluoro-2-methylphenyl azetidine · TFA) | 27 | [ES+ MS] m/z 166 (MH+). |
| 64 | (3-fluorophenyl azetidine · TFA) | 28 | [ES+ MS] m/z 152 (MH+). |
| 65 | (pyridin-4-yl azetidine · 2 TFA) See footnote a) | 29 | [ES+ MS] m/z 135 (MH+). |
| 66 | (2-fluoropyridin-4-yl azetidine · 2 TFA) See footnote a) | 30 | [ES+ MS] m/z 153 (MH+). |
| 67 | (2-chloropyridin-4-yl azetidine · 2 TFA) See footnote a) | 31 | [ES+ MS] m/z 169, 171 (MH+). |

TABLE 2-continued
| Int. | Structure | Starting Int. | Physical data |
|---|---|---|---|
| 68 | 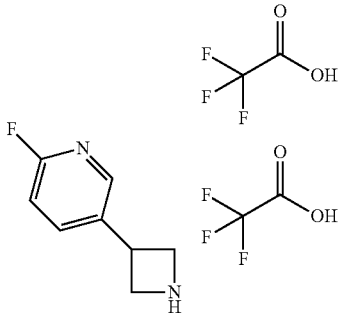 See footnote a) | 32 | [ES+ MS] m/z 153 (MH+). |
| 69 | 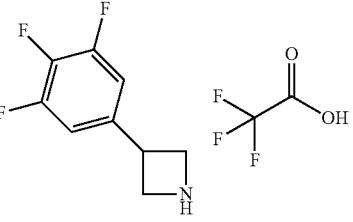 See footnote a) | 33 | [ES+ MS] m/z 188 (MH+). |
| 70 | 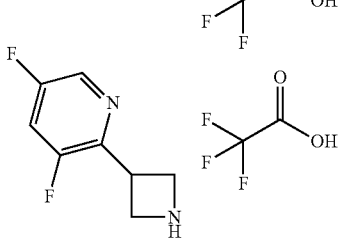 See footnote a) | 39 | [ES+ MS] m/z 171 (MH+). |
| 71 | 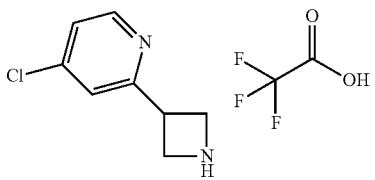 See footnote a) | 40 | [ES+ MS] m/z 169, 171 (MH+). |

TABLE 2-continued

| Int. | Structure | Starting Int. | Physical data |
|---|---|---|---|
| 72 | 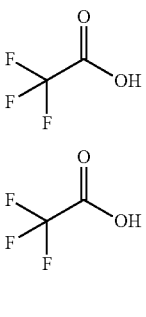 See footnote a) | 41 | [ES+ MS] m/z 203 (MH+). | a) Reaction mixture stirred at rt overnight
b) The crude material was triturated with Amberlyst A21 (5 g) during 20 min and filtered

Intermediate 73: 3-(4-chlorophenyl)azetidine Hydrochloride

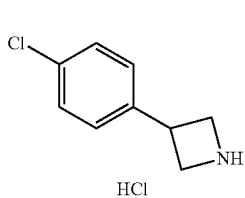 [SMILES: Clc1ccc(C2CNC2)cc1 ; Cl]

Intermediate 13 (85.0 mg, 0.32 mmol) was dissolved in DCM (1 mL) and HCl 4N in 1,4-dioxane (SIGMA-ALDRICH, 1.59 mL, 6.35 mmol) was added. The reaction mixture was stirred at rt overnight. The solvent was removed under reduced pressure to give title compound (90 mg, quant.) which was used in the next step without further purification. [ES+MS] m/z 168 (MH+).

Intermediate 74: 3-(tetrahydro-2H-pyran-4-yl)azetidine Hydrochloride

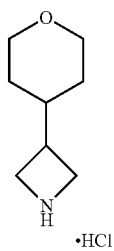

Intermediate 74 was prepared by method analogous to that described for Intermediate 73 but replacing Intermediate 13 with Intermediate 37. $^1$H NMR (400 MHz, DMSO-$d_6$) δ ppm: 8.96-8.53 (m, 2H), 3.98-3.79 (m, 4H), 3.78-3.66 (m, 2H), 3.28-3.19 (m, 2H), 2.60-2.52 (m, 1H), 1.80-1.62 (m, 1H), 1.60-1.42 (m, 2H), 1.10-0.98 (m, 2H).

Intermediate 75: 4-(azetidin-3-yl)benzonitrile Hydrochloride

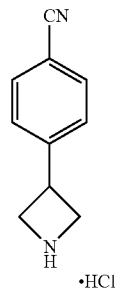

To a solution of Intermediate 34 (1.1 g, 4.258 mmol) in EtOAc (8 mL) was added HCl 4M in EtOAc (SYMAX, 8 mL) at 0° C. The reaction mixture was allowed to 26° C. and stirred for 2 h at the same temperature. The reaction mixture was concentrated under reduced pressure, the residue was washed with diethyl ether (50 mL) and dried under vacuum to yield the title compound (800 mg) as an off-white solid. $^1$H NMR (400 MHz, DMSO-$d_6$) δ ppm: 9.45 (br s, 1H), 9.18 (br s, 1H), 7.88 (d, J=8.1 Hz, 2H), 7.65 (d, J=8.3 Hz, 2H), 4.34-4.20 (m, 3H), 4.13-4.01 (m, 2H). [ES+MS] m/z 159 (MH+).

Intermediates 76-79 were prepared by methods analogous to that described for Intermediate 75 but replacing Intermediate 34 with the intermediates indicated in Table 3.

TABLE 3

| Int. | Structure | Starting Int. | Physical data |
|---|---|---|---|
| 76 | 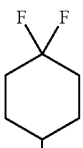 | 38 | $^1$H NMR (400 MHz, DMSO-$d_6$) δ ppm: 9.16-8.74 (m, 2H), 3.95-3.85 (m, 2H), 3.77-3.66 (m, 2H), 2.65-2.53 (m, 1H), 2.08-1.93 (m, 2H), 1.85-1.61 (m, 4H), 1.29-1.22 (m, 1H), 1.11-0.98 (m, 2H). |

TABLE 3-continued

| Int. | Structure | Starting Int. | Physical data |
|---|---|---|---|
| 77 | 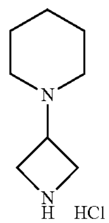 | 44 | $^1$H NMR (400 MHz, DMSO-$d_6$) δ ppm: 10.12 (br s, 1H), 9.22 (b rs, 1H), 4.58-4.44 (m, 2H), 4.30-4.16 (m, 1H), 4.15-3.99 (m, 2H) 3.37-3.24 (m, 2H), 2.89-2.71 (m, 2H), 1.90-1.61 (m, 5H), 1.47-1.26 (m, 1H). [ES+ MS] m/z 141 (MH$^+$). |
| 78 | 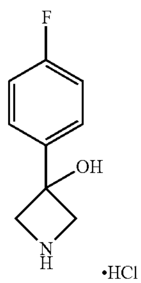 [SMILES: OC1(c2ccc(F)cc2)CNC1 ; Cl] | 45 | $^1$H NMR (400 MHz, DMSO-$d_6$) δ ppm: 9.55 (br s, 2H), 7.70-7.61 (m, 2H), 7.30-7.21 (m, 2H), 5.00 (s, 1H), 4.37-4.21 (m, 2H), 4.18-4.03 (m, 2H). [ES+ MS] m/z 168 (MH$^+$). |
| 79 | 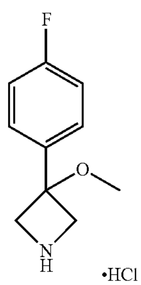 | 46 | $^1$H NMR (400 MHz, DMSO-$d_6$) δ ppm: 9.88-9.48 (m, 2H), 7.56-7.46 (m, 2H), 7.36-7.26 (m, 2H), 4.36-4.22 (m, 2H), 4.21-4.08 (m, 2H), 2.96 (s, 3H). |

Intermediate 80: 2-(4-fluorophenyl)propanenitrile

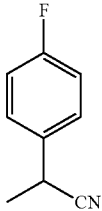

To a stirred solution of 2-(4-fluorophenyl)acetonitrile (MATRIX SCIENTIFIC, 5 g, 36.998 mmol) and methyl iodide (SYMAX FINE CHEMICALS, 2.3 mL, 36.998 mmol) in THF (100 mL) was added potassium tert-butoxide (1M in THF) (HYCHEM, 55.5 mL, 55.498 mmol) dropwise at −78° C. The reaction mixture was allowed to 27° C. and stirred for 16 h at the same temperature. The reaction mixture was quenched with saturated ammonium chloride solution (100 mL) and extracted with EtOAc (2×200 mL). Combined organic layers were dried over (anh) Na$_2$SO$_4$, filtered and concentrated under reduced pressure. The crude was purified by silica chromatography column using a linear gradient of petroleum ether/EtOAc as eluents to yield the title compound (3 g, 54%) as a pale yellow liquid. $^1$H NMR (400 MHz, CDCl$_3$) δ ppm: 7.37-7.29 (m, 2H), 7.10-7.03 (m, 2H), 3.89 (q, J=7.2 Hz, 1H), 1.63 (d, J=7.2 Hz, 3H).

Intermediate 81: 2-(4-fluorophenyl)-3-hydroxy-2-methylpropanenitrile

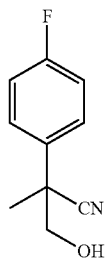

To a solution of Intermediate 80 (1 g, 6.704 mmol) and formaldehyde (FINAR, 0.8 g, 26.816 mmol) in pyridine (7 mL) was added 40% Benzyl trimethyl ammonium hydroxide in MeOH (ALFA AESAR, 2.8 mL, 6.704 mmol) dropwise at 0° C. The reaction mixture was allowed to 27° C. and stirred for 16 h at the same temperature. The reaction mixture was quenched with 1N HCl solution (20 mL) and extracted with diethyl ether (2×50 mL). Combined organic layers were dried over (anh) Na$_2$SO$_4$, filtered and the filtrate was concentrated under reduced pressure. The crude was purified by silica chromatography column using a linear gradient of petroleum ether/EtOAc as eluents to yield the title compound (600 mg, 46%) as a pale yellow thick liquid. $^1$H NMR (400 MHz, CDCl$_3$) δ ppm: 7.50-7.41 (m, 2H), 7.16-7.06 (m, 2H), 3.91-3.76 (m, 2H), 1.74 (s, 3H). [ES+MS] m/z 180 (MH$^+$).

Intermediate 82: 2-cyano-2-(4-fluorophenyl)propyl 4-methylbenzenesulfonate

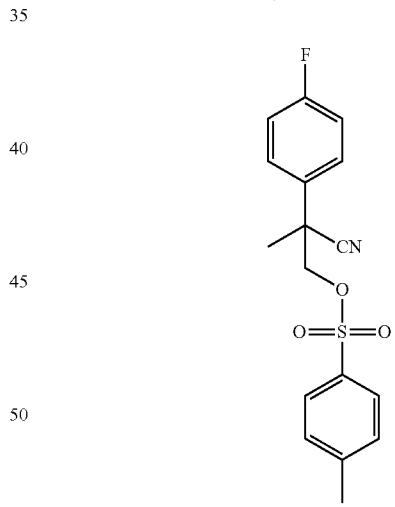

To a solution of Intermediate 81 (600 mg, 3.348 mmol) in pyridine (10 mL) was added p-toluene sulfonyl chloride (AVRA, 766 mg, 4.018 mmol) at 0° C. The reaction mixture was allowed to 27° C. and stirred for 16 h at the same temperature. The reaction mixture was quenched with 1N HCl solution (20 mL) and extracted with EtOAc (2×20 mL). Combined organic layers were washed with brine (50 mL), dried over (anh) Na$_2$SO$_4$, filtered and concentrated under reduced pressure to afford the title compound (800 mg, 65%) as a pale yellow solid. $^1$H NMR (400 MHz, CDCl$_3$) δ ppm: 7.74-7.67 (m, 2H), 7.40-7.29 (m, 4H), 7.09-7.00 (m, 2H), 4.14 (s, 2H), 2.45 (s, 3H), 1.75 (s, 3H). [ES+MS] m/z 333 (MH$^+$).

Intermediate 83: 3-(4-fluorophenyl)-3-methylazetidine

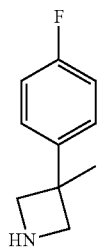

To a solution of Intermediate 82 (800 mg, 2.399 mmol) in dry THF (10 mL) was added LAH (1M in THF) (SIGMA-ALDRICH, 3.6 mL, 3.599 mmol) dropwise at 0° C. The reaction mixture was allowed to 27° C. and stirred for 4 h at the same temperature. The reaction mixture was quenched with saturated ammonium chloride solution (20 mL) and extracted with EtOAc (5×20 mL). Combined organic layers were dried over (anh) $Na_2SO_4$, filtered and concentrated under reduced pressure to yield the title compound (500 mg) as a pale yellow liquid. $^1$H NMR (400 MHz, $CDCl_3$) δ ppm: 7.74-7.68 (m, 2H), 7.15-6.89 (m, 2H), 4.40-4.32 (m, 2H), 3.99-4.05 (m, 2H), 1.78 (s, 3H). [ES+MS] m/z 166 (MH$^+$).

Intermediate 84: 4,4,4-trifluoro-1-(3-(4-fluorophenyl)-3-hydroxyazetidin-1-yl)butan-1-one

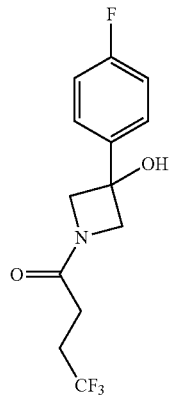 [SMILES: O=C(CCC(F)(F)F)N1CC(O)(c2ccc(F)cc2)C1]

To the solution of Intermediate 78 (500 mg, 2.455 mmol), 4,4,4-trifluorobutanoic acid (OAKWOOD, 418 mg, 2.946 mmol) in DMF (10 mL) were added DMAP (AVRA, 898 mg, 7.365 mmol) and EDC.HCl (CHEMICALS, 1.17 g, 6.138 mmol) at 0° C. The reaction mixture was allowed to 26° C. and stirred for 16 h at the same temperature. The reaction mixture was diluted with ice cold water (100 mL) and extracted with EtOAc (3×150 mL). The organic layer was washed with brine (100 mL), dried over (anh) $Na_2SO_4$, filtered and the filtrate was evaporated under reduced pressure. The crude was purified by silica chromatography column using a linear gradient of petroleum ether/EtOAc as eluents to yield the title compound (400 mg, 52.6%) as a pale yellow liquid. $^1$H NMR (400 MHz, DMSO-d$_6$) δ ppm: 7.62-7.49 (m, 2H), 7.26-7.14 (m, 2H), 6.43 (br s, 1H), 4.44-4.38 (m, 1H), 4.29-4.24 (m, 1H), 4.13-3.96 (m, 2H), 2.49-2.34 (m, 4H). [ES+MS] m/z 292 (MH$^+$).

EXAMPLES

Example 1: 4,4,4-trifluoro-1-[3-(4-fluorophenyl)azetidin-1-yl]butan-1-one

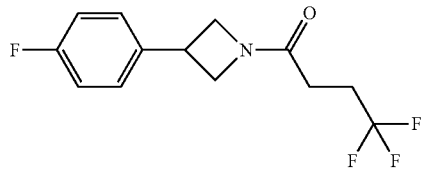

3-(4-fluorophenyl)azetidine hydrochloride (ENAMINE, 97 mg, 0.52 mmol) was suspended in chloroform (1 mL) and DMAP (SIGMA-ALDRICH, 63.3 mg, 0.52 mmol) was added. The reaction mixture was stirred at rt for 5 min and Intermediate 1 (120 mg, 0.49 mmol, 1 eq) was added. The reaction mixture was exposed to microwave irradiation for 20 min at 100° C. The reaction mixture was washed with a saturated solution of $Na_2CO_3$ (×3) then with HCl 1N solution. The organic layer was washed with brine, dried over (anh) $MgSO_4$. The residue was purified by flash chromatography on silica gel using a linear gradient of CyHex/EtOAc (from 100/0 to 50/50) to give title compound (80 mg, 59%) as a colorless oil. $^1$H NMR (300 MHz, $CD_2Cl_2$) δ ppm: 7.36-3.31 (m, 2H), 7.09 (t, J=8.7 Hz, 2H), 4.55 (t, J=8.6 Hz, 1H), 4.40 (t, J=9.3 Hz, 1H), 4.15-4.10 (m, 1H), 4.05-3.99 (m, 1H), 3.89-3.84 (m, 1H), 2.59-2.44 (m, 2H), 2.44-2.36 (m, 2H). [ES+MS] m/z 276 (MH$^+$).

Examples 2-35 were prepared by methods analogous to that described for Example 1 but replacing 3-(4-fluorophenyl)azetidine hydrochloride with that indicated in Table 4. Modifications in the protocol and in the purification step are also indicated. When examples contained a pyridine ring, the organic layer was not washed with acidic solution.

TABLE 4

| Ex. | Structure | Int. or Reagent | Physical data |
|---|---|---|---|
| 2 | ![structure] 4,4,4-trifluoro-1-[3-[3-(trifluoromethyl)phenyl]azetidin-1-yl]butan-1-one See footnote a), b) and c) | ![reagent] 0.41 mmol ENAMINE | $^1$H NMR (300 MHz, $CD_2Cl_2$) δ ppm: 7.48-7.63 (m, 4H), 4.57 (t, J = 8.6 Hz, 1H), 4.42 (t, J = 8.6 Hz, 1H), 4.12-4.20 (m, 1H), 4.00-4.11 (m, 1H), 3.87-3.99 (m, 1H), 2.34-2.62 (m, 4H). [ES+ MS] m/z 326 (MH$^+$). |

TABLE 4-continued

| Ex. | Structure | Int. or Reagent | Physical data |
|---|---|---|---|
| 3 | 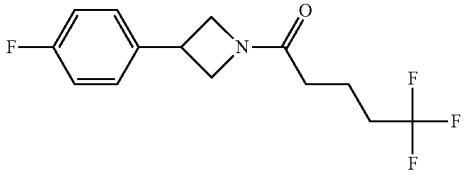<br>5,5,5-trifluoro-1-[3-(4-fluorophenyl)azetidin-1-yl]pentan-1-one<br>See footnote b), d) and m) | 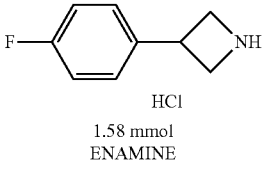 [SMILES: Fc1ccc(C2CNC2)cc1 ; Cl]<br>HCl<br>1.58 mmol<br>ENAMINE | $^1$H NMR (300 MHz, CD$_2$Cl$_2$) δ ppm: 7.28-7.33 (m, 2H), 7.03-7.10 (m, 2H), 4.49 (t, J = 8.6 Hz, 1H), 4.36 (t, J = 9.2 Hz, 1H), 4.04-4.09 (m, 1H), 3.95-4.00 (m, 1H), 3.77-3.86 (m, 1H), 2.11-2.28 (m, 4H), 1.82-1.92 (m, 2H). [ES+ MS] m/z 290 (MH$^+$). |
| 4 | 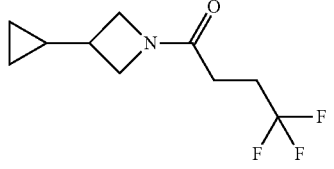<br>1-(3-cyclopropylazetidin-1-yl)-4,4,4-trifluoro-butan-1-one<br>See footnote h) | 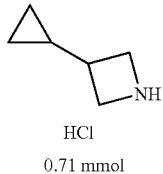<br>HCl<br>0.71 mmol<br>ENAMINE | $^1$H NMR (300 MHz, CD$_2$Cl$_2$) δ ppm: 4.17 (t, J = 8.4 Hz, 1H), 4.01 (t, J = 9.3 Hz, 1H), 3.84-3.79 (m, 1H), 3.68-3.63 (m, 1H), 2.55-2.37 (m, 2H), 2.35-2.17 (m, 3H), 1.08-0.87 (m, 1H), 0.58-0.49 (m, 2H), 0.23-0.10 (m, 2H). [ES+ MS] m/z 222 (MH$^+$). |
| 5 | 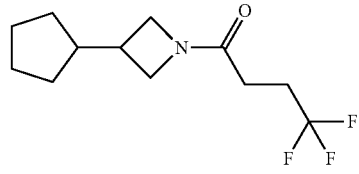<br>1-(3-cyclopentylazetidin-1-yl)-4,4,4-trifluoro-butan-1-one<br>See footnote h) | 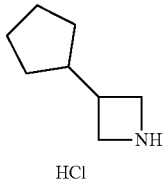<br>HCl<br>0.59 mmol<br>ENAMINE | $^1$H NMR (300 MHz, CD$_2$Cl$_2$) δ ppm: 4.15 (t, J = 8.4 Hz, 1H), 4.00 (t, J = 9.2 Hz, 1H), 3.78-3.73 m, 1H), 3.65-3.60 (m, 1H), 2.56-2.36 (m, 3H), 2.35-2.26 (m, 2H), 2.17-2.02 (m, 1H), 1.84-1.70 (m, 2H), 1.69-1.51 (m, 4H), 1.19-1.04 (m, 2H). [ES+ MS] m/z 250 (MH$^+$). |
| 6 | 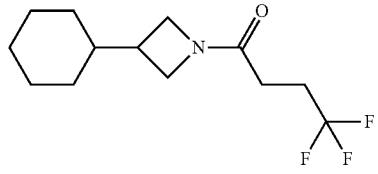<br>1-(3-cyclohexylazetidin-1-yl)-4,4,4-trifluoro-butan-1-one<br>See footnote h) | 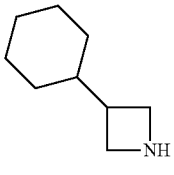<br>HCl<br>0.54 mmol<br>ENAMINE | $^1$H NMR (300 MHz, CD$_2$Cl$_2$) δ ppm: 4.12 (t, J = 8.3 Hz, 1H), 3.97 (t, J = 9.3 Hz, 1H), 3.82-3.77 (m, 1H), 3.69-3.64 (m, 1H), 2.54-2.36 (m, 2H), 2.36-2.23 (m, 3H), 1.81-1.60 (m, 5H), 1.48-1.39 (m, 1H), 1.35-1.12 (m, 3H), 0.93-0.75 (m, 2H). [ES+ MS] m/z 264 (MH$^+$). |
| 7 | 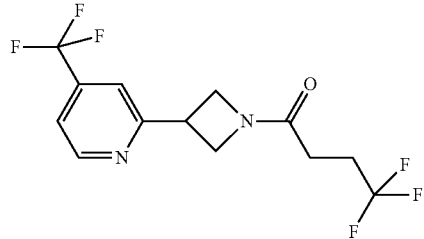<br>4,4,4-trifluoro-1-[3-[4-(trifluoromethyl)-2-pyridyl]azetidin-1-yl]butan-1-one<br>See footnote a) and e) | Int. 10<br>0.16 mmol | $^1$H NMR (300 MHz, CD$_2$Cl$_2$) δ ppm: 8.87-8.84 (m, 1H), 7.51-7.46 (m, 1H), 7.47-7.43 (m, 1H), 4.57-4.35 (m, 3H), 4.24-4.19 (m, 1H), 4.12-4.02 (m, 1H), 2.61-2.37 (m, 4H). [ES+ MS] m/z 327 (MH$^+$). |

TABLE 4-continued

| Ex. | Structure | Int. or Reagent | Physical data |
|---|---|---|---|
| 8 | 4,4,4-trifluoro-1-[3-[5-(trifluoromethyl)-2-pyridyl]azetidin-1-yl]butan-1-one<br>See footnote a) and e) | Int. 11<br>0.18 mmol | $^1$H NMR (300 MHz, CD$_2$Cl$_2$) δ ppm: 8.94-8.91 (m, 1H), 7.98-7.91 (m, 1H), 7.40-7.37 (m, 1H), 4.57-4.36 (m, 3H), 4.24-4.19 (m, 1H), 4.11-4.04 (m, 1H), 2.62-2.45 (m, 2H), 2.45-2.36 (m, 2H). [ES+ MS] m/z 327 (MH$^+$). |
| 9 | 4,4,4-trifluoro-1-[3-(5-fluoro-2-pyridyl)azetidin-1-yl]butan-1-one<br>See footnote f) and g) | Int. 47<br>0.41 mmol | $^1$H NMR (300 MHz, CD$_2$Cl$_2$) δ ppm: 8.50 (d, J = 2.9 Hz, 1H), 7.45-7.38 (m, 1H), 7.25-7.20 (m, 1H), 4.50-4.45 (m, 1H), 4.41-4.31 (m, 2H), 4.17-4.12 (m, 1H), 4.02-3.92 (m, 1H), 2.59-2.36 (m, 4H). [ES+ MS] m/z 277 (MH$^+$). |
| 10 | 1-[3-(3,5-difluoro-2-pyridyl)azetidin-1-yl]-4,4,4-trifluoro-butan-1-one<br>See footnote i) and j) | Int. 70<br>1.05 mmol | $^1$H NMR (300 MHz, CD$_2$Cl$_2$) δ ppm: 8.40 (d, J = 2.4 Hz, 1H), 7.23-7.31 (m, 1H), 4.49 (d, J = 6.7 Hz, 2H), 4.39-4.32 (m, 1H), 4.28-4.18 (m, 2H), 2.59-2.44 (m, 2H), 2.43-2.36 (m, 3H). [ES+ MS] m/z 295 (MH$^+$). |
| 11 | 1-[3-(4-chloro-2-pyridyl)azetidin-1-yl]-4,4,4-trifluoro-butan-1-one<br>See footnote i) and j) | Int. 71<br>1.14 mmol | $^1$H NMR (300 MHz, CD$_2$Cl$_2$) δ ppm: 8.57-8.55 (m, 1H), 7.29-7.26 (m, 2H), 4.52-4.33 (m, 3H), 4.20-4.15 (m, 1H), 4.00-3.90 (m, 1H), 2.60-2.37 (m, 4H). [ES+ MS] m/z 293, 295 (MH$^+$). |
| 12 | 4,4,4-trifluoro-1-[3-[2-(trifluoromethyl)-4-pyridyl]azetidin-1-yl]butan-1-one<br>See footnote i) and j) | Int. 72<br>0.21 mmol | $^1$H NMR (300 MHz, CD$_2$Cl$_2$) δ ppm: 8.73 (d, J = 5.1 Hz, 1H), 7.67 (d, J = 1.6 Hz, 1H), 7.50-7.48 (m, 1H), 4.61 (t, J = 8.6 Hz, 1H), 4.47 (t, J = 9.3 Hz, 1H), 4.21-4.16 (m, 1H), 4.10-4.04 (m, 1H), 4.00-3.90 (m, 1H), 2.60-2.37 (m, 4H). [ES+ MS] m/z 327 (MH$^+$). |

TABLE 4-continued

| Ex. | Structure | Int. or Reagent | Physical data |
|---|---|---|---|
| 13 | 1-[3-(4-chlorophenyl)azetidin-1-yl]-4,4,4-trifluoro-butan-1-one<br>See footnote d) | Int. 73<br>0.32 mmol | $^1$H NMR (300 MHz, CD$_2$Cl$_2$) δ ppm: 7.38 (d, J = 8.5 Hz, 2H), 7.30 (d, J = 8.5 Hz, 2H), 4.57-4.51 m, 1H), 4.43-4.37 (m, 1H), 4.14-4.09 (m, 1H), 4.03-3.98 (m, 1H), 3.90-3.82 (m, 1H), 2.61-2.37 (m, 3H). [ES+ MS] m/z 292, 294 (MH$^+$). |
| 14 | 4,4,4-trifluoro-1-[3-[4-(trifluoromethoxy)phenyl]azetidin-1-yl]butan-1-one<br>See footnote d) | Int. 49<br>0.25 mmol | $^1$H NMR (300 MHz, CDCl$_3$) δ ppm: 7.36-7.31 (m, 2H), 7.22 (d, J = 8.7 Hz, 2H), 4.57 (t, J = 8.8 Hz, 1H), 4.44 (t, J = 9.4 Hz, 1H), 4.18-4.11 (m, 1H), 4.11-4.04 (m, 1H), 3.92-3.81 (m, 1H), 2.60-2.42 (m, 2H), 2.42-2.33 (m, 2H). [ES+ MS] m/z 342 (MH$^+$). |
| 15 | 4,4,4-trifluoro-1-[3-[3-(trifluoromethoxy)phenyl]azetidin-1-yl]butan-1-one<br>See footnote d) | Int. 50<br>0.15 mmol | $^1$H NMR (300 MHz, CD$_2$Cl$_2$) δ ppm: 7.23-7.13 (m, 4H), 3.66-3.62 (m, 2H), 3.50-3.46 (m, 2H), 2.87 (s, 4H), 2.65-2.45 (m, 4H), 1.68-1.60 (m, 4H). [ES+ MS] m/z 342 (MH$^+$). |
| 16 | 4,4,4-trifluoro-1-[3-[4-(trifluoromethoxy)phenyl]azetidin-1-yl]butan-1-one<br>See footnote a) and d) | Int. 51<br>0.68 mmol | $^1$H NMR (300 MHz, CD$_2$Cl$_2$) δ ppm: 7.67 (d, J = 8.2 Hz, 2H), 7.49 (d, J = 8.2 Hz, 2H), 4.59 (t, J = 8.6 Hz, 1H), 4.44 (t, J = 9.3 Hz, 1H), 4.19-4.14 (m, 1H), 4.09-4.04 (m, 1H), 3.99-3.89 (m, 1H), 2.61-2.45 (m, 2H), 2.45-2.36 (m, 2H). [ES+ MS] m/z 326 (MH$^+$). |
| 17 | 1-[3-(3-chlorophenyl)azetidin-1-yl]-4,4,4-trifluoro-butan-1-one<br>See footnote a) and d) | Int. 52<br>0.92 mmol | $^1$H NMR (300 MHz, CDCl$_3$) δ ppm: 7.40-7.33 (m, 2H), 7.33-7.27 (m, 1H), 7.30-7.24 (m, 1H), 4.56 (t, J = 8.6 Hz, 1H), 4.42 (t, J = 9.4 Hz, 1H), 4.18-4.10 (m, 1H), 4.08-3.98 (m, 1H), 3.91-3.80 (m, 1H), 2.61-2.44 (m, 2H), 2.44-2.36 (m, 2H). [ES+ MS] m/z 292, 294 (MH$^+$). |

TABLE 4-continued

| Ex. | Structure | Int. or Reagent | Physical data |
|---|---|---|---|
| 18 | 1-[3-(2,4-difluorophenyl)azetidin-1-yl]-4,4,4-trifluoro-butan-1-one<br>See footnote a) and d) | Int. 53<br>0.44 mmol | $^1$H NMR (300 MHz, CD$_2$Cl$_2$) δ ppm: 7.40-7.30 (m, 1H), 6.99-6.92 (m, 1H), 6.92-6.84 (m, 1H), 4.54 (t, J = 8.4 Hz, 1H), 4.39 (t, J = 8.4 Hz, 1H), 4.20 (t, J = 8.1 Hz, 1H), 4.14-4.01 (m, 2H), 2.59-2.42 (m, 2H), 2.42-2.34 (m, 2H). [ES+ MS] m/z 294 (MH$^+$). |
| 19 | 1-[3-(2,4-difluorophenyl)azetidin-1-yl]-4,4,4-trifluoro-butan-1-one<br>See footnote d) and i) | Int. 54<br>0.95 mmol | $^1$H NMR (300 MHz, CD$_2$Cl$_2$) δ ppm: 8.36-8.31 (m, 1H), 7.75-7.68 (m, 1H), 7.43-7.36 (m, 1H), 4.59 (t, J = 8.9 Hz, 1H), 4.45 (t, J = 8.9 Hz, 1H), 4.16-4.12 (m, 1H), 4.06-4.00 (m, 1H), 3.95-3.84 (m, 1H), 2.61-2.44 (m, 2H), 2.44-2.36 (m, 2H). [ES+ MS] m/z 293 (MH$^+$). |
| 20 | 1-[3-(2-chloro-4-fluoro-phenyl)azetidin-1-yl]-4,4,4-trifluoro-butan-1-one<br>See footnote d) | Int. 55<br>0.58 mmol | $^1$H NMR (300 MHz, CD$_2$Cl$_2$) δ ppm: 7.44-7.37 (m, 1H), 7.22-7.16 (m, 1H), 7.13-7.05 (m, 1H), 4.59 (t, J = 6.6 Hz, 1H), 4.41 (t, J = 8.8 Hz, 1H), 4.26-4.08 (m, 3H), 2.59-2.43 (m, 2H), 2.43-2.34 (m, 2H). [ES+ MS] m/z 310 (MH$^+$). |
| 21 | 4,4,4-trifluoro-1-[3-[6-(trifluoromethoxy)-3-pyridyl]azetidin-1-yl]butan-1-one<br>See footnote d) | Int. 56<br>1.07 mmol | $^1$H NMR (300 MHz, CD$_2$Cl$_2$) δ ppm: 8.68 (d, J = 2.0 Hz, 1H), 7.95-7.91 (m, 1H), 7.74 (d, J = 8.1 Hz, 1H), 4.64 (t, J = 8.7 Hz, 1H), 4.48 (t, J = 9.4 Hz, 1H), 4.22-4.17 (m, 1H), 4.10-4.05 (m, 1H), 4.01-3.95 (m, 1H), 2.60-2.44 (m, 2H), 2.44-2.36 (m, 2H). [ES+ MS] m/z 327 (MH$^+$). |
| 22 | 4,4,4-trifluoro-1-[3-[6-methoxyl-3-pyridyl)azetidin-1-yl]butan-1-one<br>See footnote d) and i) | Int. 57<br>0.94 mmol | $^1$H NMR (300 MHz, CD$_2$Cl$_2$) δ ppm: 8.08 (d, J = 2.6 Hz, 1H), 7.66-7.63 (m, 1H), 6.80 (d, J = 8.6 Hz, 1H), 4.55 (t, J = 8.7 Hz, 1H), 4.40 (t, J = 9.1 Hz, 1H), 4.14-4.09 (m, 1H), 4.03-3.97 (m, 1H), 3.93 (s, 3H), 3.86-3.80 (m, 1H), 2.60-2.43 (m, 2H), 2.43-2.35 (m, 2H). [ES+ MS] m/z 289 (MH$^+$). |

TABLE 4-continued

| Ex. | Structure | Int. or Reagent | Physical data |
|---|---|---|---|
| 23 | 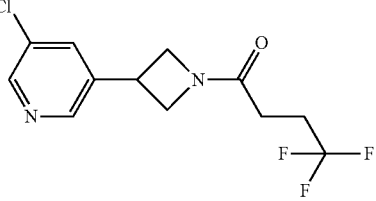
1-[3-(5-chloro-3-pyridyl)azetidin-1-yl]-4,4,4-trifluoro-butan-1-one
See footnote d) and i) | Int. 58
0.91 mmol | $^1$H NMR (300 MHz, CD$_2$Cl$_2$) δ ppm: 8.50 (d, J = 2.2 Hz, 1H), 8.45 (d, J = 2.2 Hz, 1H), 7.93 (t, J = 2.2 Hz, 1H), 4.60 (t, J = 8.8 Hz, 1H), 4.44 (t, J = 9.4 Hz, 1H), 4.19-4.15 (m, 1H), 4.07-4.02 (m, 1H), 3.93-3.87 (m, 1H), 2.60-2.44 (m, 2H), 2.44-2.36 (m, 2H). [ES+ MS] m/z 293, 295 (MH$^+$). |
| 24 | 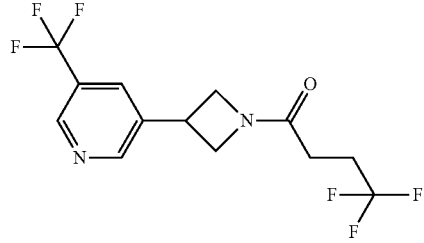
4,4,4-trifluoro-1-[3-[5-(trifluoromethyl)-3-pyridyl]azetidin-1-yl]butan-1-one
See footnote d) and i) | Int. 59
0.29 mmol | $^1$H NMR (300 MHz, CD$_2$Cl$_2$) δ ppm: 8.84 (d, J = 2.1 Hz, 1H), 8.80 (d, J = 2.1 Hz, 1H), 7.97 (t, J = 2.1 Hz, 1H), 7.74 (d, J = 8.1 Hz, 1H), 4.64 (t, J = 8.6 Hz, 1H), 4.50 (t, J = 9.4 Hz, 1H), 4.23-4.18 (m, 1H), 4.12-4.05 (m, 1H), 4.03-3.97 (m, 1H), 2.62-2.46 (m, 2H), 2.46-2.38 (m, 2H). [ES+ MS] m/z 327 (MH$^+$). |
| 25 | 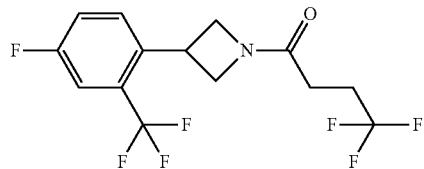
4,4,4-trifluoro-1-[3-[5-fluoro-2-(trifluoromethyl)phenyl]azetidin-1-yl]butan-1-one
See footnote d) | Int. 60
0.22 mmol | $^1$H NMR (300 MHz, CD$_2$Cl$_2$) δ ppm: 7.74 (dd, J = 8.6 Hz, 5.2 Hz, 1H), 7.46-7.36 (m, 2H), 4.57 (t, J = 8.6 Hz, 1H), 4.41 (t, J = 9.1 Hz, 1H), 4.32-4.22 (m, 1H), 4.16-4.08 (m, 2H), 2.61-2.44 (m, 2H), 2.44-2.36 (m, 2H). [ES+ MS] m/z 344 (MH$^+$). |
| 26 | 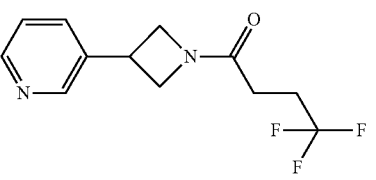
4,4,4-trifluoro-1-[3-(3-pyridyl)azetidin-1-yl]butan-1-one
See footnote k) and i) | Int. 61
0.77 mmol | $^1$H NMR (300 MHz, CD$_2$Cl$_2$) δ ppm: 8.56 (d, J = 2.1 Hz, 1H), 8.54-8.52 (m, 1H), 7.75-7.69 (m, 1H), 7.37-7.33 (m, 2H), 4.58 (t, J = 8.9 Hz, 1H), 4.44 (t, J = 9.4 Hz, 1H), 4.19-4.14 (m, 1H), 4.09-4.03 (m, 1H), 3.94-3.84 (m, 1H), 2.60-2.45 (m, 2H), 2.45-2.36 (m, 2H). [ES+ MS] m/z 259 (MH$^+$). |

TABLE 4-continued

| Ex. | Structure | Int. or Reagent | Physical data |
|---|---|---|---|
| 27 | 1-[3-(3,4-difluorophenyl)azetidin-1-yl]-4,4,4-trifluorobutan-1-one<br>See footnote k) | Int. 62<br>0.52 mmol | $^1$H NMR (300 MHz, CD$_2$Cl$_2$) δ ppm: 7.27-7.16 (m, 2H), 7.13-7.06 (m, 1H), 4.56 (t, J = 8.6 Hz, 1H), 4.41 (t, J = 9.3 Hz, 1H), 4.14-4.09 (m, 1H), 4.03-3.98 (m, 1H), 3.88-3.82 (m, 1H), 2.61-2.43 (m, 2H), 2.43-2.35 (m, 2H). [ES+ MS] m/z 294 (MH$^+$). |
| 28 | 4,4,4-trifluoro-1-[3-(4-fluoro-2-methylphenyl)azetidin-1-yl]butan-1-one<br>See footnote k) | Int. 63<br>0.49 mmol | $^1$H NMR (300 MHz, CD$_2$Cl$_2$) δ ppm: 7.37-7.32 (m, 1H), 7.02-6.91 (m, 2H), 4.55 (t, J = 7.8 Hz, 1H), 4.45-4.45 (m, 1H), 4.21-4.14 (m, 1H), 4.12-4.00 (m, 1H), 2.60-2.44 (m, 2H), 2.44-2.35 (m, 2H), 2.26 (s, 3H). [ES+ MS] m/z 290 (MH$^+$). |
| 29 | 4,4,4-trifluoro-1-[3-(3-fluorophenyl)azetidin-1-yl]butan-1-one<br>See footnote k) | Int. 64<br>1.14 mmol | $^1$H NMR (300 MHz, CD$_2$Cl$_2$) δ ppm: 7.42-7.33 (m, 1H), 7.14 (d, J = 7.8 Hz, 1H), 7.10-7.05 (m, 1H), 7.05-6.97 (m, 1H), 4.55 (t, J = 8.7 Hz, 1H), 4.41 (t, J = 9.4 Hz, 1H), 4.18-4.11 (m, 1H), 4.07-4.00 (m, 1H), 3.93-3.82 (m, 1H), 2.60-2.42 (m, 2H), 2.42-2.34 (m, 2H). [ES+ MS] m/z 276 (MH$^+$). |
| 30 | 4,4,4-trifluoro-1-[3-(4-pyridyl)azetidin-1-yl]butan-1-one<br>See footnote k) and i) | Int. 65<br>0.29 mmol | $^1$H NMR (300 MHz, CD$_2$Cl$_2$) δ ppm: 8.64 (d, J = 4.3 Hz, 2H), 7.38 (d, J = 4.3 Hz, 2H), 4.59 (t, J = 8.6 Hz, 1H), 4.44 (t, J = 9.3 Hz, 1H), 4.21-4.14 (m, 1H), 4.10-4.03 (m, 1H), 3.96-3.85 (m, 1H), 2.60-2.43 (m, 2H), 2.43-2.36 (m, 2H). [ES+ MS] m/z 259 (MH$^+$). |
| 31 | 4,4,4-trifluoro-1-[3-(2-fluoro-4-pyridyl)azetidin-1-yl]butan-1-one<br>See footnote k) and i) | Int. 66<br>0.32 mmol | $^1$H NMR (300 MHz, CD$_2$Cl$_2$) δ ppm: 8.22 (d, J = 5.2 Hz, 1H), 7.20-7.15 (m, 1H), 6.91 (d, J = 1.7 Hz, 1H), 4.59 (t, J = 8.9 Hz, 1H), 4.44 (t, J = 9.5 Hz, 1H), 4.19-4.12 (m, 1H), 4.08-4.00 (m, 1H), 3.95-3.84 (m, 1H), 2.60-2.44 (m, 2H), 2.44-2.35 (m, 2H). [ES+ MS] m/z 277 (MH$^+$). |

TABLE 4-continued

| Ex. | Structure | Int. or Reagent | Physical data |
|---|---|---|---|
| 32 | 1-[3-(2-chloro-4-pyridyl)azetidin-1-yl]-4,4,4-trifluoro-butan-1-one<br>See footnote k) and i) | Int. 67<br>0.86 mmol | $^1$H NMR (300 MHz, CD$_2$Cl$_2$) δ ppm: 8.36 (d, J = 5.3 Hz, 1H), 7.30 (brs, 1H), 7.23-7.19 (m, 1H), 4.55 (t, J = 8.7 Hz, 1H), 4.40 (t, J = 9.6 Hz, 1H), 4.18-4.11 (m, 1H), 4.06-3.99 (m, 1H), 3.90-3.78 m, 1H), 2.58-2.42 (m, 2H), 2.42-2.33 (m, 2H). [ES+ MS] m/z 293, 295 (MH$^+$). |
| 33 | 4,4,4-trifluoro-1-[3-(6-fluoro-3-pyridyl)azetidin-1-yl]butan-1-one<br>See footnote k) and i) | Int. 68<br>0.94 mmol | $^1$H NMR (300 MHz, CD$_2$Cl$_2$) δ ppm: 8.12 (d, J = 2.6 Hz, 1H), 7.85-7.79 (m, 1H), 6.99-6.95 (m, 1H), 4.55 (t, J = 8.7 Hz, 1H), 4.41 (t, J = 9.4 Hz, 1H), 4.13-4.08 (m, 1H), 4.02-3.97 (m, 1H), 3.92-3.82 (m, 1H), 2.57-2.33 (m, 4H). [ES+ MS] m/z 277 (MH$^+$). |
| 34 | 4,4,4-trifluoro-1-[3-(3,4,5-trifluorophenyl)azetidin-1-yl]butan-1-one<br>See footnote k) | Int. 69<br>0.99 mmol | $^1$H NMR (300 MHz, CD$_2$Cl$_2$) δ ppm: 7.05-6.94 (m, 2H), 4.54 (t, J = 8.7 Hz, 1H), 4.40 (t, J = 9.6 Hz, 1H), 4.11-4.05 (m, 1H), 4.01-3.93 (m, 1H), 3.86-3.75 (m, 1H), 2.59-2.41 (m, 2H), 2.41-2.34 (m, 2H). [ES+ MS] m/z 312 (MH$^+$). |
| 35 | 1-[3-(4,4-difluoro-1-piperidyl)azetidin-1-yl]-4,4,4-trifluoro-butan-1-one<br>See footnote f) and l) | Int. 48<br>0.69 mmol | $^1$H NMR (300 MHz, CD$_2$Cl$_2$) δ ppm: 4.17-4.12 (m, 1H), 4.04-4.01 (m, 1H), 3.99-3.93 (m, 1H), 3.83-3.78 (m, 1H), 3.26-3.21 m, 1H), 2.52-2.39 (m, 6H), 2.36-2.30 (m, 2H), 2.09-1.96 (m, 4H). [ES+ MS] m/z 301 (MH$^+$). | a) The reaction was performed without DMAP
b) 15 min at 100° C.
c) Purification on silica gel (CyHex/EtOAc 90/10 to 50/50)
d) Purification by preparative HPLC (OmniSpher C18 column, 10μ, 41 × 250 mm) gradient 15 min 10% to 100% ACN/H$_2$O (0.1% formic acid)
e) Purification by preparative HPLC (XBridge C18 column, 5μ, 30 × 150 mm) gradient 20 min 10% to 50% ACN/H$_2$O (pH = 9, ammonium formate)
f) 3 eq DMAP
g) Purification by preparative HPLC (OmniSpher C18 column, 10μ, 41 × 250 mm) gradient 30 min 10% to 100% ACN/H$_2$O (0.1% formic acid)
h) Purification on silica gel ( (DCM/MeOH 100/0 to 99/1)
i) 2 eq DMAP
j) Purification by preparative HPLC (OmniSpher C18 column, 10μ, 41 × 250 mm) gradient 19 min 10% to 100% ACN/H$_2$O (0.1% formic acid)
k) Purification by preparative HPLC (OmniSpher C18 column, 10μ, 41 × 250 mm) gradient 35 min 10% to 100% ACN/H$_2$O (0.1% formic acid)
l) Purification by preparative HPLC (OmniSpher C18 column, 10μ, 41 × 250 mm) gradient 25 min 10% to 100% ACN/H$_2$O (0.1% formic acid)
m) Example 3 was prepared by method analogous to that described for Example 1 but using intermediate 2 instead of intermediate 1

Example 36: 4,4,4-trifluoro-1-[3-(6-isopropoxy-3-pyridyl)azetidin-1-yl]butan-1-one

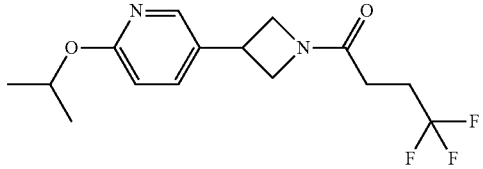 [SMILES: CC(C)Oc1ccc(C2CN(C(=O)CCC(F)(F)F)C2)cn1]

To a solution of NaH (SIGMA-ALDRICH, 15.2 mg, 0.634 mmol) in (anh) THF (1.4 mL) was added propan-2-ol (SIGMA-ALDRICH, 0.048 mL, 0.634 mmol) at 0° C. under argon. After 10 min Example 33 (35 mg, 0.127 mmol) was added at rt and the reaction mixture was heated at reflux 80° C. overnight. The reaction was monitoring by LCMS. A new solution of NaH (15.2 mg, 0.634 mmol, 5) in (anh) THF (1.40 mL) with propan-2-ol (0.048 mL, 0.634 mmol) at 0° C. under argon was added to the reaction mixture. The reaction mixture was heated again at reflux 80° C. overnight. The reaction mixture was quenched with brine/water (50/50) followed by water. The aq. layer was extracted with EtOAc (×3). Then the organic layer was dried over (anh) MgSO$_4$, filtered and evaporated in vacuo. The residue was purified by preparative HPLC (XBridge C18 column, 5μ, 10×150 mm) gradient 20 min 0% to 98% ACN/H$_2$O (pH=3.8, ammonium formate) to give title compound (10 mg, 25%) as an yellow oil. $^1$H NMR (300 MHz, CD$_2$Cl$_2$) δ ppm: 8.01 (d, J=2.6 Hz, 1H), 7.60-7.56 (m, 1H), 6.68 (d, J=8.6 Hz, 1H), 5.30-5.20 (m, 1H), 4.5 (t, J=8.4 Hz, 1H), 4.36 (t, J=9.2 Hz, 1H), 4.09-4.05 (m, 1H), 3.99-3.93 (m, 1H), 3.83-3.73 (m, 1H), 2.56-2.32 (m, 4H), 1.31 (d, J=6.2 Hz, 6H). [ES+MS] m/z 317 (MH$^+$).

Example 37: 4,4,4-trifluoro-1-[3-[6-(2,2,2-trifluoroethoxy)-3-pyridyl]azetidin-1-yl]butan-1-one

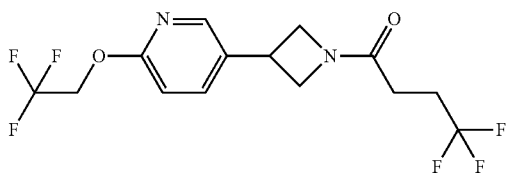 [SMILES: O=C(CCC(F)(F)F)N1CC(c2ccc(OCC(F)(F)F)nc2)C1]

Example 37 was prepared by method analogous to that described for Example 36 from Example 33 (0.16 mmol) but replacing the propan-2-ol with 2,2,2-trifluoroethanol (SIGMA-ALDRICH, 0.81 mmol). $^1$H NMR (300 MHz, CD$_2$Cl$_2$) δ ppm: 8.05 (d, J=2.5 Hz, 1H), 7.72-7.68 (m, 1H), 6.90 (d, J=8.5 Hz, 1H), 4.78 (q, J=8.7 Hz, 2H), 4.52 (t, J=8.6 Hz, 1H), 4.38 (t, J=9.3 Hz, 1H), 4.11-4.06 (m, 1H), 4.01-3.95 (m, 1H), 3.87-3.77 (m, 1H), 2.56-2.33 (m, 4H). [ES+MS] m/z 357 (MH$^+$).

Example 38: 4,4,4-trifluoro-1-(3-(tetrahydro-2H-pyran-4-yl)azetidin-1-yl)butan-1-one

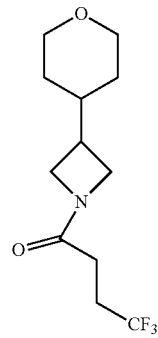 [SMILES: O=C(CCC(F)(F)F)N1CC(C2CCOCC2)C1]

To a solution of 4,4,4-trifluorobutanoic acid (OAKWOOD, 337 mg, 2.3728 mmol) in DCM (3.3 mL) were added oxalyl chloride (AVRA, 251 mg, 1.977 mmol) and catalytic mount of DMF at 27° C. The reaction mixture was stirred for 2 h at the same temperature. To the mixture of Intermediate 74 (350 mg, 1.977 mmol), saturated sodium bicarbonate solution (6.2 mL) and EtOAc (3.3 mL), the above reaction mixture was added at 0° C. The reaction mixture was allowed to 27° C. and stirred for 16 h at the same temperature. The reaction mixture was poured into saturated sodium bicarbonate solution (50 mL) and extracted with EtOAc (3×50 mL). The organic was dried over (anh) Na$_2$SO$_4$, filtered and concentrated under reduced pressure. The crude was purified by silica chromatography column using a linear gradient of DCM/MeOH as eluents. The obtained compound was purified by preparative HPLC (X SELECT C18 column, 5μ, 19×150 mm) gradient 15 min 0% to 15% ACN/NH$_4$HCO$_3$ (aq. 10 mM) to afford the title compound (95 mg, 18%) as a white gum. $^1$H NMR (400 MHz, DMSO-d$_6$) δ ppm: 4.17-4.09 (m, 1H), 3.90-3.80 (m, 4H), 3.61-3.54 (m, 1H), 3.28-3.19 (m, 2H), 2.48-2.37 (m, 2H), 2.36-2.24 (m, 3H), 1.70-1.59 (m, 1H), 1.57-1.48 (m, 2H), 1.15-1.00 (m, 2H). [ES+MS] m/z 266 (MH$^+$).

Example 39: 4,4,4-trifluoro-1-(3-(piperidin-1-yl)azetidin-1-yl)butan-1-one

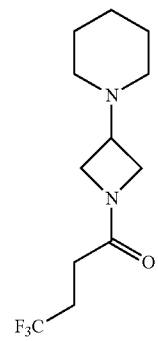

To a solution of Intermediate 79 (500 mg, 2.84 mmol), 4,4,4-trifluorobutanoic acid (OAKWOOD, 484 mg, 3.409 mmol) in DMF (10 mL) were added DMAP (AVRA, 1.03 g, 8.522 mmol), and EDC.HCl (VINSA, 1.35 g, 7.102 mmol) in portionwise at 0° C. The resultant reaction mixture was allowed to 26° C. and stirred for 16 h at the same temperature. The reaction mixture was diluted with ice cold water (50 mL) and extracted with ethyl EtOAc (3×150 mL). Combined organic layers were washed with brine solution (150 mL), dried over (anh) $Na_2SO_4$, filtered and concentrated under reduced pressure. The crude was purified by silica chromatography column using a linear gradient of petroleum ether/EtOAc as eluents to yield the title compound (120 mg, 15%). $^1$H NMR (400 MHz, $CDCl_3$) δ ppm: 4.15-4.09 (m, 1H), 4.05-3.95 (m, 2H), 3.91-3.85 (m, 1H), 3.16-3.04 (m, 1H), 2.53-2.13 (m, 8H), 1.64-1.57 (m, 4H), 1.52-1.43 (m, 2H). [ES+MS] m/z 265 (MH+).

Examples 40-42 were prepared by methods analogous to that described for Example 39, replacing Intermediate 77 with Intermediates indicated in Table 5. Modifications in the purification step are also indicated.

TABLE 5

| Ex. | Structure | Int. | Physical data |
|---|---|---|---|
| 40 | 1-(3-(4,4-difluorocyclohexyl)azetidin-1-yl)-4,4,4-trifluorobutan-1-one<br>See footnote a) | 76<br>0.6616<br>mmol | $^1$H NMR (400 MHz, $CDCl_3$) δ ppm: 4.22-4.15 (m, 1H), 4.10-4.03 (m, 1H), 3.85-3.79 (m, 1H), 3.75-3.69 (m, 1H), 2.54-2.35 (m, 3H), 2.34-2.26 (m, 2H), 2.19-2.06 (m, 2H), 1.81-1.61 (m, 4H), 1.54-1.46 (m, 1H), 1.30-1.14 (m, 2H). [ES+ MS] m/z 300 (MH+). |
| 41 | 4,4,4-trifluoro-1-(3-(4-fluorophenyl)-3-methoxyazetidin-1-yl)butan-1-one<br>See footnote b) | 79<br>3.215<br>mmol | $^1$H NMR (400 MHz, $CDCl_3$) δ ppm: 7.39-7.31 (m, 2H), 7.16-7.08 (m, 2H), 4.39-4.20 (m, 4H), 3.07 (s, 3H), 2.56-2.31 (m, 4H). [ES+ MS] m/z 306 (MH+). |
| 42 | 4,4,4-trifluoro-1-(3-(4-fluorophenyl)-3-methylazetidin-1-yl)butan-1-one<br>See footnote b) | 83<br>3.026<br>mmol | $^1$H NMR (400 MHz, $CDCl_3$) δ ppm: 7.21-7.14 (m, 2H), 7.09-7.02 (m, 2H), 4.37-4.24 (m, 2H), 4.14-4.00 (m, 2H), 2.57-2.31 (m, 4H), 1.65 (s, 3H). [ES+ MS] m/z 290 (MH+). | a) Purification by preparative HPLC (X Bridge C18 column, 5µ, 19 × 150 mm) gradient 15 min 0% to 10% ACN/$NH_4HCO_3$ (aq. 10 mM)
b) Purification using a linear gradient of petroleum ether/AcOEt Example 43: 4-(1-(4,4-trifluorobutanoyl)azetidin-3-yl)benzonitrile

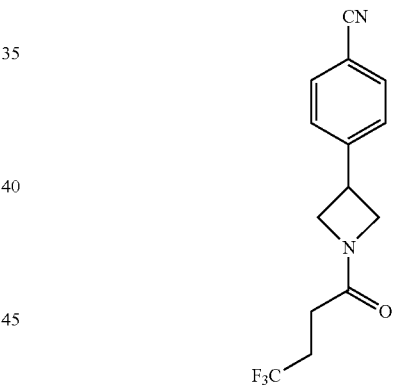

To a solution of Intermediate 75 (800 mg, 4.102 mmol) in DMF (15 mL) were added EDC.HCl (SILVARY, 1.95 g, 10.256 mmol), 4,4,4-trifluorobutanoic acid (OAKWOOD, 699 mg, 4.923 mmol) at 0° C., followed by the addition of DMAP (AVRA, 1.5 g, 12.307 mmol) at 0° C. The resultant reaction mixture was allowed to 26° C. and stirred for 16 h at the same temperature. The reaction mixture was diluted with ice cold water (200 mL) and extracted with EtOAc (3×150 mL). Combined organic layers were washed with brine solution (100 mL), dried over (anh) $Na_2SO_4$, filtered and concentrated under reduced pressure. The crude was purified by silica chromatography column using a linear gradient of petroleum ether/EtOAc as eluents to yield the title compound (500 mg, 42%) as a colorless gum. $^1$H NMR (400 MHz, $CDCl_3$) δ ppm: 7.71-7.65 (m, 2H), 7.45-7.39 (m, 2H), 4.64-4.42 (m, 2H), 4.20-4.05 (m, 2H), 3.94-3.87 (m, 1H), 2.58-2.43 (m, 2H), 2.41-2.34 (m, 2H). [ES+MS] m/z 283 (MH+).

Example 44: 4,4,4-trifluoro-1-(3-fluoro-3-(4-fluorophenyl)azetidin-1-yl)butan-1-one

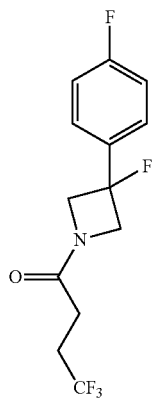 [SMILES: O=C(CCC(F)(F)F)N1CC(F)(c2ccc(F)cc2)C1]

To the solution of Intermediate 84 (400 mg, 1.373 mmol) in DCM (5 mL) was added a solution of DAST (ALFA AESAR, 0.18 mL, 1.373 mmol) in DCM (5 mL) in dropwise at −78° C. and stirred for 1 h. The reaction mixture temperature was allowed to 26° C. and stirred for 30 min at the same temperature. The reaction mixture was quenched with saturated sodium bicarbonate solution (100 mL) and extracted with DCM (3×100 mL). The organic layer was washed with brine (100 mL), dried over (anh) $Na_2SO_4$, filtered and concentrated under reduced pressure. The crude was purified by silica chromatography column using a linear gradient of petroleum ether/EtOAc as eluents and obtained compound which was further purified by preparative HPLC (Kromosil C18 column, 10p, 21.2×250 mm) gradient 17 min 0% to 30% ACN/$NH_4HCO_3$ (aq. 10 mM) to afford the title compound (61 mg, 14.8%) as a colorless gum. $^1$H NMR (400 MHz, $CDCl_3$) δ ppm: 7.46-7.39 (m, 2H), 7.18-7.09 (m, 2H), 4.67-4.34 (m, 4H), 2.60-2.36 (m, 4H). [ES+MS] m/z 294 (MH$^+$).

Biological Activity

Measurement of Growth Inhibition of *M. tuberculosis* GFP Strains by Combination of Ethionamide (ETH) and Examples 1-11

1. Construction of Mycobacterial Recombinant Strains.
   Strain *M. tuberculosis* H37Rv-GFP.

A recombinant strain of *M. tuberculosis* H37Rv expressing the green fluorescent protein (H37Rv-GFP) was obtained by transformation of the integrative plasmid pNIP48 (Abadie et al., 2005; Cremer et al., 2002). In this plasmid derived from the Ms6 mycobacteriophage, the GFP gene was cloned under the strong mycobacterial promoter pBlaF and the GFP was constitutively expressed. This plasmid also contained an hygromycin resistance gene.

Strain *M. tuberculosis* W4-E1-GFP (Mutant).

The *M. tuberculosis* strain E1 was a derivative of the Beijing strain W4 that was selected on ethionamide-containing agar plates (20 μg/ml). This strain carries a Gly343Ala mutation in EthA. The W4-E1 strain was transformed using pNIP48 as described above to give the fluorescent strain W4-E1-GFP.

2. Growth and Preparation of the Fluorescent Mycobacteria

Bacterial stocks kept at −80° C. were used to inoculate 5 ml of Middlebrook 7H9 medium supplemented with oleic acid-albumin-dextrose-catalase (OADC, Difco, Sparks Md., USA) and with 50 μg ml$^{-1}$ hygromycin (Invitrogen, Carlsbad, Calif. USA) in 25 cm$^2$ tissue-culture flasks. Flasks were incubated at 37° C. without shaking for 7 days. Cultures were then diluted with fresh culture medium to reach an $OD_{600}$ of 0.1. Culture flasks (75 cm$^2$) were filled with 50 ml of this diluted culture, which were cultivated 7 days at 37° C. without shaking.

3. Microplates Preparation

Ethionamide (Sigma, E6005) was diluted in DMSO at 0.1 mg/mL and 0.8 mg/ml; aliquots were stored frozen at −20° C. Test-compounds were resuspended in DMSO at a final concentration of 10 μM. Ethionamide and test-compounds were transferred to a 384-well low-volume polypropylene plate (Corning, no. 3672) and used to prepare assay plates. Ten 3-fold serial dilutions of compounds (typically in the ranges of 30 to 4.5e-3 μM) were performed into black Greiner 384-well clear bottom polystyrene plates (Greiner, no. 781091) using an Echo 550 liquid Handler (Labcyte). DMSO volume was compensated so that the concentration across all wells was equal (0.3%).

Ethionamide was then transferred to the 384-well plates, using Echo. The final concentration of ETH was 0.1 μg/ml for assays involving H37Rv-GFP, and was 0.8 μg/ml for assays involving W4-E1-GFP. The final amount of DMSO in the assay plate remained <1% v/v for each well.

Controls in the assay plate include DMSO at 0.3% (negative control) and INH at 1 μg/ml (positive control). A reference plate included rifampicin, INH and ETH ranging from 30 to 1.8e-3 μg/ml (15 points, 2× dilutions).

Cultures of H37Rv-GFP or of W4-E1-GFP to be added to assay plates were washed two times in PBS (Gibco, 14190), resuspended in fresh culture medium (without Hygromycin), and grown for 5 days at 37° C.

Finally, cultures were diluted to an OD600 nm of 0.02 (using fresh culture medium with no added Hygromycin) and 50 μL were transferred to each assay plate. Assay plates were incubated at 37° C. for 5 days. Fluorescent signal was acquired on a Victor 3 multilabel plate reader (Perkin Elmer), using exc=485 nm/em=535 nm.

Results

All Example compounds were tested essentially according to the procedure described above and found to have the activity values reported below.

EC50_H37Rv measures the ability of the compounds of the invention to potentiate ethionamide activity against H37Rv strains, whereas EC50_Mutant measures the ability of the compounds of the invention to potentiate ethionamide activity against strains of TB that are resistant to ethionamide.

| Example number | EC50_H37Rv | EC50_Mutant |
| --- | --- | --- |
| 1 | +++++ | +++++ |
| 2 | +++++ | ++++ |
| 3 | +++++ | ++++ |
| 4 | +++ | ++ |
| 5 | +++++ | ++++ |
| 6 | +++++ | +++++ |
| 7 | ++++ | +++ |
| 8 | +++ | ++ |
| 9 | ++++ | ++ |
| 10 | +++++ | +++ |
| 11 | ++++ | ++++ |
| 12 | +++ | + |
| 13 | +++++ | ++++ |
| 14 | +++++ | + |
| 15 | +++++ | ++++ |

| Example number | EC50_H37Rv | EC50_Mutant |
|---|---|---|
| 16 | ++++ | +++ |
| 17 | +++++ | +++++ |
| 18 | +++++ | +++++ |
| 19 | +++ | + |
| 20 | ++++ | ++++ |
| 21 | + | + |
| 22 | +++++ | ++++ |
| 23 | +++ | + |
| 24 | + | + |
| 25 | ++++ | +++ |
| 26 | + | + |
| 27 | +++++ | +++++ |
| 28 | ++++ | +++ |
| 29 | +++++ | ++++ |
| 30 | + | + |
| 31 | ++ | + |
| 32 | +++ | + |
| 33 | ++ | + |
| 34 | +++++ | ++++ |
| 35 | ++ | ++ |
| 36 | ++++ | + |
| 37 | +++ | + |
| 38 | +++ | + |
| 39 | + | + |
| 40 | ++++ | ++++ |
| 41 | +++++ | ++++ |
| 42 | +++++ | ++++ |
| 43 | + | + |
| 44 | +++++ | +++++ |

<50 nM = +++++
≥50 nM to <250 nM = ++++
≥250 nM to <500 nM = +++
≥500 nM to <1.0 µM (≥500 nM to <1000 nM) = ++
≥1.0 µM to ≤10 µM (≥1000 nM to ≤10,000 nM) = +

In particular, Examples 6, 17, 18, 34 and 45 were found to have an average EC50_H37Rv of ≤10 nM and an average EC50_Mutant of <75 nM.

*Mycobacterium tuberculosis* In Vitro H37Rv in Human Macrophaqes THP-1 Inhibition Assay (Intracellular Assay)

Intracellular screening is a valuable tool for identifying new anti-tuberculosis compounds that are active in human macrophages. This ex-vivo assay may represent physiological conditions that mimic disease and take into consideration the favorable contribution of host cells. (Sorrentino, F. et al. (2016) Antimicrob. Agents Chemother. 60 (1), 640-645.)

Procedure was carried out as described in Sorrentino, F. et al. (2016) Antimicrob. Agents Chemother. 60 (1), 640-645 (supplemental material), except that before THP-1 infected cells were seeded in 384 well plates, infected macrophages were filtered in the last step of wash steps with a 40 um cell strainer to remove cell clumps and obtain single cell suspension.

The compounds of the examples were tested essentially in accordance with the above-mentioned assay (without the presence of ethionamide). The results are provided in the Table below.

| Example Number | IC50 (µM) |
|---|---|
| 1 | +++++ |
| 2 | +++++ |
| 3 | ++++ |
| 4 | ++++ |
| 7 | ++++ |
| 8 | + |
| 9 | ++++ |
| 11 | ++++ |
| 12 | ++++ |
| 13 | ++++ |
| 14 | +++ |
| 15 | +++++ |
| 16 | +++ |
| 17 | +++++ |
| 18 | +++++ |
| 19 | ++++ |
| 20 | ++++ |
| 21 | +++ |
| 23 | +++++ |
| 25 | ++++ |
| 26 | + |
| 28 | ++++ |
| 29 | +++++ |
| 34 | ++++ |
| 38 | ++++ |
| 41 | +++++ |
| 42 | +++++ |

<50 nM = +++++
≥50 nM to <250 nM = ++++
≥250 nM to <500 nM = +++
≥500 nM to <1.0 µM (≥500 nM to <1000 nM) = ++
≥1.0 µM to ≤10 µM (≥1000 nM to ≤10,000 nM) = +

The invention claimed is:

1. A compound of Formula (I) or pharmaceutically acceptable salt thereof

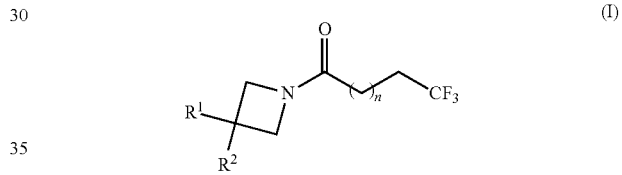

(I)

wherein
n is 1 or 2;
$R^1$ is hydrogen, fluoro, methyl or methoxy; and
$R^2$ is phenyl, pyridyl, $C_{3-6}$ cycloalkyl, piperidin-1-yl or tetrahydropyranyl, wherein phenyl and pyridyl are optionally substituted by one to three substituents independently selected from chloro, fluoro, cyano, $C_{1-3}$ alkyl optionally substituted by one or more fluoro, or $C_{1-3}$ alkoxy optionally substituted by one or more fluoro, and cycloalkyl, piperidin-1-yl and tetrahydropyranyl are optionally substituted by one or two fluoro.

2. The compound or pharmaceutically acceptable salt thereof according to claim 1, wherein n is 1.

3. The compound or pharmaceutically acceptable salt thereof according to claim 1, wherein $R^1$ is hydrogen.

4. The compound or pharmaceutically acceptable salt thereof according to claim 1, wherein $R^2$ is phenyl, pyridyl or $C_{3-6}$ cycloalkyl,
wherein phenyl and pyridyl are optionally substituted by one to three substituents independently selected from chloro, fluoro, methyl optionally substituted by one or more fluoro, or methoxy substituted by one or more fluoro, and cycloalkyl is unsubstituted.

5. The compound or pharmaceutically acceptable salt thereof according to claim 1, wherein $R^2$ is phenyl, pyridyl or $C_{3-6}$ cycloalkyl,
wherein phenyl and pyridyl are optionally substituted by one to three substituents independently selected from chloro, fluoro, methyl, trifluoromethyl, methoxy or trifluoromethoxy, and cycloalkyl is unsubstituted.

6. The compound or pharmaceutically acceptable salt thereof according to claim 1, wherein $R^2$ is phenyl, pyridyl or $C_{3-6}$ cycloalkyl,
   wherein phenyl and pyridyl are optionally substituted by one to three substituents independently selected from chloro and fluoro, and cycloalkyl is unsubstituted.

7. The compound or pharmaceutically acceptable salt thereof according to claim 1, wherein $R^1$ is fluoro, methyl or methoxy.

8. The compound or pharmaceutically acceptable salt thereof according to claim 1, wherein $R^2$ is phenyl optionally substituted by one to three substituents independently selected from chloro, fluoro, cyano, $C_{1-3}$ alkyl optionally substituted by one or more fluoro, or $C_{1-3}$ alkoxy optionally substituted by one or more fluoro.

9. The compound or pharmaceutically acceptable salt thereof according to claim 8, wherein $R^2$ is phenyl optionally substituted by one fluoro.

10. The compound or pharmaceutically acceptable salt thereof according to claim 1 selected from:
    4,4,4-trifluoro-1-[3-(4-fluorophenyl)azetidin-1-yl]butan-1-one;
    4,4,4-trifluoro-1-[3-[3-(trifluoromethyl)phenyl]azetidin-1-yl]butan-1-one;
    5,5,5-trifluoro-1-[3-(4-fluorophenyl)azetidin-1-yl]pentan-1-one;
    1-(3-cyclopropylazetidin-1-yl)-4,4,4-trifluoro-butan-1-one;
    1-(3-cyclopentylazetidin-1-yl)-4,4,4-trifluoro-butan-1-one;
    1-(3-cyclohexylazetidin-1-yl)-4,4,4-trifluoro-butan-1-one;
    4,4,4-trifluoro-1-[3-[4-(trifluoromethyl)-2-pyridyl]azetidin-1-yl]butan-1-one;
    4,4,4-trifluoro-1-[3-[5-(trifluoromethyl)-2-pyridyl]azetidin-1-yl]butan-1-one;
    4,4,4-trifluoro-1-[3-(5-fluoro-2-pyridyl)azetidin-1-yl]butan-1-one;
    1-[3-(3,5-difluoro-2-pyridyl)azetidin-1-yl]-4,4,4-trifluoro-butan-1-one;
    1-[3-(4-chloro-2-pyridyl)azetidin-1-yl]-4,4,4-trifluoro-butan-1-one;
    4,4,4-trifluoro-1-[3-[2-(trifluoromethyl)-4-pyridyl]azetidin-1-yl]butan-1-one;
    1-[3-(4-chlorophenyl)azetidin-1-yl]-4,4,4-trifluoro-butan-1-one;
    4,4,4-trifluoro-1-[3-[4-(trifluoromethoxy)phenyl]azetidin-1-yl]butan-1-one;
    4,4,4-trifluoro-1-[3-[3-(trifluoromethoxy)phenyl]azetidin-1-yl]butan-1-one;
    4,4,4-trifluoro-1-[3-[4-(trifluoromethoxy)phenyl]azetidin-1-yl]butan-1-one;
    1-[3-(3-chlorophenyl)azetidin-1-yl]-4,4,4-trifluoro-butan-1-one;
    1-[3-(2,4-difluorophenyl)azetidin-1-yl]-4,4,4-trifluoro-butan-1-one;
    1-[3-(2,4-difluorophenyl)azetidin-1-yl]-4,4,4-trifluoro-butan-1-one;
    1-[3-(2-chloro-4-fluoro-phenyl)azetidin-1-yl]-4,4,4-trifluoro-butan-1-one;
    4,4,4-trifluoro-1-[3-[6-(trifluoromethyl)-3-pyridyl]azetidin-1-yl]butan-1-one;
    4,4,4-trifluoro-1-[3-(6-methoxy-3-pyridyl)azetidin-1-yl]butan-1-one;
    1-[3-(5-chloro-3-pyridyl)azetidin-1-yl]-4,4,4-trifluoro-butan-1-one;
    4,4,4-trifluoro-1-[3-[5-(trifluoromethyl)-3-pyridyl]azetidin-1-yl]butan-1-one;
    4,4,4-trifluoro-1-[3-[4-fluoro-2-(trifluoromethyl)phenyl]azetidin-1-yl]butan-1-one;
    4,4,4-trifluoro-1-[3-(3-pyridyl)azetidin-1-yl]butan-1-one;
    1-[3-(3,4-difluorophenyl)azetidin-1-yl]-4,4,4-trifluoro-butan-1-one;
    4,4,4-trifluoro-1-[3-(4-fluoro-2-methyl-phenyl)azetidin-1-yl]butan-1-one;
    4,4,4-trifluoro-1-[3-(3-fluorophenyl)azetidin-1-yl]butan-1-one;
    4,4,4-trifluoro-1-[3-(4-pyridyl)azetidin-1-yl]butan-1-one;
    4,4,4-trifluoro-1-[3-(2-fluoro-4-pyridyl)azetidin-1-yl]butan-1-one;
    1-[3-(2-chloro-4-pyridyl)azetidin-1-yl]-4,4,4-trifluoro-butan-1-one;
    4,4,4-trifluoro-1-[3-(6-fluoro-3-pyridyl)azetidin-1-yl]butan-1-one;
    4,4,4-trifluoro-1-[3-(3,4,5-trifluorophenyl)azetidin-1-yl]butan-1-one;
    1-[3-(4,4-difluoro-1-piperidyl)azetidin-1-yl]-4,4,4-trifluoro-butan-1-one;
    4,4,4-trifluoro-1-[3-(6-isopropoxy-3-pyridyl)azetidin-1-yl]butan-1-one;
    4,4,4-trifluoro-1-[3-[6-(2,2,2-trifluoroethoxy)-3-pyridyl]azetidin-1-yl]butan-1-one;
    4,4,4-trifluoro-1-(3-(tetrahydro-2H-pyran-4-yl)azetidin-1-yl)butan-1-one;
    1-(3-(4,4-difluorocyclohexyl)azetidin-1-yl)-4,4,4-trifluorobutan-1-one;
    4,4,4-trifluoro-1-(3-(piperidin-1-yl)azetidin-1-yl)butan-1-one;
    4,4,4-trifluoro-1-(3-(4-fluorophenyl)-3-methoxyazetidin-1-yl)butan-1-one;
    4,4,4-trifluoro-1-(3-(4-fluorophenyl)-3-methylazetidin-1-yl)butan-1-one;
    4-(1-(4,4,4-trifluorobutanoyl)azetidin-3-yl)benzonitrile; and
    4,4,4-trifluoro-1-(3-fluoro-3-(4-fluorophenyl)azetidin-1-yl)butan-1-one.

11. The method for the treatment of a mycobacterial infection in a human in need thereof, comprising administering to said human a therapeutically effective amount of the compound or a pharmaceutically acceptable salt thereof according to claim 1.

12. A method for the treatment of a disease caused by infection with a *Mycobacterium* in a human in need thereof, comprising administering to said human a therapeutically effective amount of the compound or a pharmaceutically acceptable salt thereof according to claim 1.

13. A pharmaceutical composition comprising (a) a compound or pharmaceutically acceptable salt thereof according to claim 1; and (b) a pharmaceutically acceptable excipient.

14. A combination of (a) the compound or pharmaceutically acceptable according to claim 1 and (b) at least one other anti-mycobacterial agent.

15. The combination according to claim 14, wherein the at least one other anti-mycobacterial agent is an anti-tuberculosis agent.

16. The combination according to claim 15, wherein the anti-tuberculosis agent is selected from isoniazid, rifampin, pyrazinamide, ethambutol, moxifloxacin, rifapentine, clofazimine, ethionamide, prothionamide, isoxyl, thiacetazone, rifabutin, a diarylquinoline, nitroimidazo-oxazine PA-824, delamanid (OPC-67683), an oxazolidinone, EMB analogue SQ109, OPC-167832, GSK3036656 (also known as GSK070), GSK2556286, GSK3211830, a benzothiazinone, an azaindole, a dinitrobenzamide, and a beta-lactam, or beta-lactam combinations.

17. The combination according to claim 14, further comprising an antiviral agent.

18. The combination according to claim 17, wherein the antiretroviral agent is selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

19. A method for the treatment of tuberculosis in a human in need thereof, comprising administering to said human a therapeutically effective amount the compound, or pharmaceutically acceptable salt thereof according to claim 1.

20. The method according to claim 11, wherein the mycobacterial infection is a *Mycobacterium tuberculosis* infection.

21. The method according to claim 12, wherein the disease caused by infection with a *Mycobacterium* is a *Mycobacterium tuberculosis* infection.

22. A method for the treatment of a mycobacterial infection in a human in need thereof, comprising administering to said human (a) the compound or pharmaceutically acceptable salt thereof according to claim 1; and (b) at least one other anti-mycobacterial agent.

23. The method according to claim 22, wherein the at least one other anti-mycobacterial agent is an anti-tuberculosis agent.

24. The method according to claim 23, wherein the anti-tuberculosis agent is selected from isoniazid, rifampin, pyrazinamide, ethambutol, moxifloxacin, rifapentine, clofazimine, ethionamide, prothionamide, isoxyl, thiacetazone, a diarylquinoline, nitroimidazo-oxazine PA-824 (pretomanid), delamanid (OPC-67683), an oxazolidinone, EMB analogue SQ109, OPC-167832, GSK3036656A (also known as GSK070), GSK2556286, GSK3211830, a benzothiazinone, an azaindole, a dinitrobenzamide, and a beta-lactam, or beta-lactam combinations.

25. The method according to claim 22, further comprising an antiviral agent.

26. The method according to claim 25, wherein the antiretroviral agent is selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

\* \* \* \* \*